US011717641B2

(12) United States Patent
Giles

(10) Patent No.: US 11,717,641 B2
(45) Date of Patent: Aug. 8, 2023

(54) MEDICAL DEVICE WITH DISTAL TORQUE CONTROL

(71) Applicant: Micronovus, LLC, Dallas, TX (US)

(72) Inventor: Brian Giles, Dallas, TX (US)

(73) Assignee: MicroNovus, LLC, Dallas, TX (US)

( * ) Notice: Subject to any disclaimer, the term of this patent is extended or adjusted under 35 U.S.C. 154(b) by 868 days.

(21) Appl. No.: 16/551,454

(22) Filed: Aug. 26, 2019

(65) Prior Publication Data

US 2019/0374745 A1 Dec. 12, 2019

Related U.S. Application Data

(63) Continuation of application No. 15/204,800, filed on Jul. 7, 2016, now Pat. No. 10,391,274.

(51) Int. Cl.
*A61M 25/00* (2006.01)
*A61M 25/01* (2006.01)
*A61M 25/09* (2006.01)
*A61B 90/00* (2016.01)
(Continued)

(52) U.S. Cl.
CPC ...... *A61M 25/0012* (2013.01); *A61M 25/005* (2013.01); *A61M 25/013* (2013.01); *A61M 25/0127* (2013.01); *A61M 25/09041* (2013.01); *A61B 1/00064* (2013.01); *A61B 5/061* (2013.01); *A61B 2090/031* (2016.02); *A61M 25/0133* (2013.01); *A61M 25/0138* (2013.01)

(58) Field of Classification Search
CPC ............ A61M 25/0012; A61M 25/005; A61M 25/013; A61M 25/0127; A61M 25/09041; A61M 25/0133; A61M 25/0138; A61M 25/0144; A61M 25/0147; A61M 25/0054; A61M 25/0053; A61M 2025/0004; A61B 2017/00309
See application file for complete search history.

(56) References Cited

U.S. PATENT DOCUMENTS 3,674,014 A 7/1972 Tillander
4,321,931 A 3/1982 Hon
4,545,390 A 10/1985 Leary
(Continued)

FOREIGN PATENT DOCUMENTS

JP 2000-126301 5/2000
JP 2012-531270 12/2012
(Continued)

OTHER PUBLICATIONS

Product Brochure in 2 pages for SPIROL® Spring-Reinforced Epidural Catheter (retrieved on or about Feb. 25, 2016 from http://www.bd.com/anesthesia/products/epidural_twist.asp).
(Continued)

*Primary Examiner* — Devin B Henson
(74) *Attorney, Agent, or Firm* — Knobbe, Martens, Olson & Bear, LLP

(57) ABSTRACT

A catheter with a distal end that rotates through the conversion of linear motion to rotational motion, thus the distal end may be rotated without longitudinally advancing or retracting the distal end. The catheter includes a tube with a single helix or a dual chirality helix cut into the tube, a distal end segment, means for linear displacement of the helix, and means for coupling the junction point of the helix to the distal segment.

20 Claims, 19 Drawing Sheets

(51) Int. Cl.
*A61B 1/00* (2006.01)
*A61B 5/06* (2006.01)

(56) References Cited

U.S. PATENT DOCUMENTS

| | | | |
|---|---|---|---|
| 4,548,206 A | 10/1985 | Osborne | |
| 4,619,274 A | 10/1986 | Morrison | |
| 4,721,117 A | 1/1988 | Mar et al. | |
| 4,757,827 A | 7/1988 | Buchbinder et al. | |
| 4,790,831 A | 12/1988 | Skribiski | |
| 4,867,173 A | 9/1989 | Leoni | |
| 4,867,174 A | 9/1989 | Skribiski | |
| 4,925,445 A | 5/1990 | Sakamoto et al. | |
| 4,960,410 A | 10/1990 | Pinchuk | |
| 5,040,543 A | 8/1991 | Badera et al. | |
| 5,052,404 A | 10/1991 | Hodgson | |
| 5,095,915 A | 3/1992 | Engelson | |
| 5,171,383 A | 12/1992 | Sagae et al. | |
| 5,228,453 A | 7/1993 | Sepetka | |
| 5,269,757 A | 12/1993 | Fagan et al. | |
| 5,329,923 A | 7/1994 | Lundquist | |
| RE34,695 E | 8/1994 | Mar et al. | |
| 5,365,943 A | 11/1994 | Jansen | |
| 5,507,751 A | 4/1996 | Goode et al. | |
| 5,570,701 A | 11/1996 | Ellis et al. | |
| 5,573,520 A | 11/1996 | Schwartz et al. | |
| 5,599,492 A | 2/1997 | Engelson | |
| 5,605,543 A | 2/1997 | Swanson | |
| 5,741,429 A | 4/1998 | Donadio, III et al. | |
| 5,743,876 A | 4/1998 | Swanson | |
| 5,762,615 A | 6/1998 | Weier | |
| 5,772,609 A | 6/1998 | Nguyen et al. | |
| 5,843,153 A | 12/1998 | Johnston et al. | |
| 5,897,529 A | 4/1999 | Ponzi | |
| 5,961,510 A | 10/1999 | Fugoso et al. | |
| 5,984,877 A | 11/1999 | Fleischhacker, Jr. | |
| 6,001,068 A | 12/1999 | Uchino et al. | |
| 6,019,736 A | 2/2000 | Avellanet et al. | |
| 6,022,343 A | 2/2000 | Johnson et al. | |
| 6,048,338 A | 4/2000 | Larson et al. | |
| 6,053,922 A | 4/2000 | Krause et al. | |
| 6,132,388 A | 10/2000 | Fleming et al. | |
| 6,213,974 B1 | 4/2001 | Smith et al. | |
| 6,306,105 B1 | 10/2001 | Rooney et al. | |
| 6,385,472 B1 | 5/2002 | Hall et al. | |
| 6,475,167 B1 | 11/2002 | Fleming et al. | |
| 6,475,209 B1 | 11/2002 | Larson et al. | |
| 6,482,217 B1 | 11/2002 | Pintor et al. | |
| 6,575,920 B2 | 6/2003 | Zhou | |
| 6,579,246 B2 | 6/2003 | Jacobsen et al. | |
| 6,594,517 B1 | 7/2003 | Nevo | |
| 6,602,262 B2 | 8/2003 | Griego et al. | |
| 6,605,086 B2 | 8/2003 | Hayzelden et al. | |
| 6,682,493 B2 | 1/2004 | Mirigian | |
| 6,716,183 B2 | 4/2004 | Clayman et al. | |
| 6,834,201 B2 | 12/2004 | Gillies et al. | |
| 6,881,194 B2 | 4/2005 | Miyata et al. | |
| 6,890,329 B2 | 5/2005 | Carroll et al. | |
| 7,044,921 B2 | 5/2006 | Asmus et al. | |
| 7,077,811 B2 | 7/2006 | Vrba et al. | |
| 7,117,703 B2 | 10/2006 | Kato et al. | |
| 7,182,735 B2 | 2/2007 | Shireman et al. | |
| 7,211,082 B2 | 5/2007 | Hall et al. | |
| 7,235,088 B2 | 6/2007 | Pintor et al. | |
| 7,276,062 B2 | 10/2007 | McDaniel et al. | |
| 7,316,656 B2 | 1/2008 | Shireman et al. | |
| 7,344,546 B2 | 3/2008 | Wulfman et al. | |
| 7,381,198 B2 | 6/2008 | Noriega et al. | |
| 7,470,239 B1 | 12/2008 | Rooney et al. | |
| 7,485,127 B2 | 2/2009 | Nistal | |
| 7,488,338 B2 | 2/2009 | Eidenschink | |
| 7,615,032 B2 | 11/2009 | Whittaker et al. | |
| 7,618,379 B2 | 11/2009 | Reynolds et al. | |
| 7,641,621 B2 | 1/2010 | Crank | |
| 7,674,272 B2 | 3/2010 | Torrance et al. | |
| 7,691,103 B2 | 4/2010 | Fernandez et al. | |
| 7,708,704 B2 | 5/2010 | Mitelberg et al. | |
| 7,713,231 B2 | 5/2010 | Wulfman et al. | |
| 7,747,314 B2 | 6/2010 | Parins et al. | |
| 7,758,591 B2 | 7/2010 | Griego et al. | |
| 7,763,012 B2 | 7/2010 | Petrick et al. | |
| 7,771,388 B2 | 8/2010 | Olsen et al. | |
| 7,776,062 B2 | 8/2010 | Besselink et al. | |
| 7,780,611 B2 | 8/2010 | Griego et al. | |
| 7,811,294 B2 | 10/2010 | Strommer et al. | |
| 7,842,055 B2 | 11/2010 | Pintor et al. | |
| 7,867,176 B2 | 1/2011 | Wu et al. | |
| 7,878,984 B2 | 2/2011 | Jacobsen et al. | |
| 7,887,529 B2 | 2/2011 | Eder | |
| 7,892,186 B2 | 2/2011 | Soukup et al. | |
| 7,892,233 B2 | 2/2011 | Hall et al. | |
| 7,946,999 B2 | 5/2011 | Rooney et al. | |
| 7,955,272 B2 | 6/2011 | Rooney et al. | |
| 7,993,286 B2 | 8/2011 | Reynolds et al. | |
| 7,998,088 B2 | 8/2011 | Vrba et al. | |
| 7,998,090 B2 | 8/2011 | Simpson et al. | |
| 7,998,132 B2 | 8/2011 | Gregorich et al. | |
| 8,055,327 B2 | 11/2011 | Strommer et al. | |
| 8,137,336 B2 | 3/2012 | Ostrovsky et al. | |
| 8,167,821 B2 | 5/2012 | Sharrow | |
| 8,222,566 B2 | 7/2012 | Shireman et al. | |
| 8,231,647 B2 | 7/2012 | Eidenschink | |
| 8,267,873 B2 | 9/2012 | Yanuma | |
| 8,292,827 B2 | 10/2012 | Musbach et al. | |
| 8,292,829 B2 | 10/2012 | Griego et al. | |
| 8,303,570 B2 | 11/2012 | Gregorich et al. | |
| 8,313,493 B2 | 11/2012 | Fischer | |
| 8,323,240 B2 | 12/2012 | Wulfman et al. | |
| 8,353,850 B2 | 1/2013 | Ressemann et al. | |
| 8,372,056 B2 | 2/2013 | Jimenez et al. | |
| 8,372,056 B2 | 2/2013 | Eder | |
| 8,376,963 B2 | 2/2013 | Wright et al. | |
| 8,382,786 B2 | 2/2013 | Besselink et al. | |
| 8,388,572 B2 | 3/2013 | Olsen et al. | |
| 8,388,629 B2 | 3/2013 | Griego et al. | |
| 8,394,091 B2 | 3/2013 | Rioux et al. | |
| 8,414,477 B2 | 4/2013 | Tallarida et al. | |
| 8,414,506 B2 | 4/2013 | Reynolds et al. | |
| 8,425,532 B2 | 4/2013 | Flom et al. | |
| 8,449,526 B2 | 5/2013 | Snyder et al. | |
| 8,454,537 B2 | 6/2013 | Simpson et al. | |
| 8,460,214 B2 | 6/2013 | Kuban et al. | |
| 8,480,668 B2 | 7/2013 | Fernandez et al. | |
| 8,556,914 B2 | 10/2013 | Vrba et al. | |
| 8,579,926 B2 | 11/2013 | Pintor et al. | |
| 8,608,726 B2 | 12/2013 | Whittaker et al. | |
| 8,672,837 B2 | 3/2014 | Roelle et al. | |
| 8,684,953 B2 | 4/2014 | Cabiri | |
| 8,708,953 B2 | 4/2014 | Salahieh et al. | |
| 8,721,564 B2 | 5/2014 | Simpson et al. | |
| 8,764,743 B2 | 7/2014 | McDaniel et al. | |
| 8,771,288 B2 | 7/2014 | Griego et al. | |
| 8,814,848 B2 | 8/2014 | Gregorich et al. | |
| 8,845,552 B2 | 9/2014 | Griego et al. | |
| 8,894,610 B2 | 11/2014 | Macnamara et al. | |
| 8,920,369 B2 | 12/2014 | Salahieh et al. | |
| 8,951,224 B2 | 2/2015 | Wulfman et al. | |
| 8,968,383 B1 | 3/2015 | Johnson et al. | |
| 9,138,566 B2 | 9/2015 | Cabiri | |
| 9,192,285 B2 | 11/2015 | Ostrovsky et al. | |
| 9,421,343 B2 | 8/2016 | Berthiaume et al. | |
| 9,474,639 B2 | 10/2016 | Haggstrom et al. | |
| 9,492,103 B2 | 11/2016 | Strommer et al. | |
| 9,498,363 B2 | 11/2016 | Watson et al. | |
| 9,586,025 B2 | 3/2017 | Salahieh et al. | |
| 9,636,482 B2 | 5/2017 | McDaniel et al. | |
| 9,649,473 B2 | 5/2017 | Gregorich et al. | |
| 9,808,867 B2 * | 11/2017 | Krause | A61B 17/1631 |
| 9,918,705 B2 | 3/2018 | Giles | |
| 10,391,274 B2 | 8/2019 | Giles | |
| 10,441,746 B2 | 10/2019 | Besselink | |
| 10,786,230 B2 | 9/2020 | Giles | |
| 11,141,141 B2 | 10/2021 | Giles | |
| 2002/0072662 A1 | 6/2002 | Hall et al. | |

(56) References Cited

U.S. PATENT DOCUMENTS

| | | |
|---|---|---|
| 2002/0103430 A1 | 8/2002 | Hastings et al. |
| 2003/0009208 A1 | 1/2003 | Snyder et al. |
| 2004/0059257 A1 | 3/2004 | Gaber |
| 2004/0236312 A1 | 11/2004 | Nistal et al. |
| 2005/0283179 A1 | 12/2005 | Lentz |
| 2006/0014418 A1 | 1/2006 | Kato et al. |
| 2006/0089569 A1 | 4/2006 | Soukup et al. |
| 2006/0100687 A1 | 5/2006 | Fahey et al. |
| 2006/0184105 A1* | 8/2006 | Townsend ......... A61M 25/0141 604/93.01 |
| 2007/0123805 A1 | 5/2007 | Shireman et al. |
| 2007/0185415 A1 | 8/2007 | Ressemann et al. |
| 2007/0225739 A1 | 9/2007 | Pintor et al. |
| 2008/0228208 A1 | 9/2008 | Wulfman et al. |
| 2009/0157048 A1 | 6/2009 | Sutermeister et al. |
| 2009/0306587 A1 | 12/2009 | Milijasevic et al. |
| 2010/0069882 A1 | 3/2010 | Jennings et al. |
| 2010/0114151 A1 | 5/2010 | Mujwid et al. |
| 2010/0324576 A1 | 12/2010 | Pintor et al. |
| 2010/0331776 A1 | 12/2010 | Salahieh et al. |
| 2012/0179097 A1 | 7/2012 | Cully et al. |
| 2013/0072904 A1 | 3/2013 | Musbach et al. |
| 2013/0116705 A1 | 5/2013 | Salahieh et al. |
| 2013/0158516 A1 | 6/2013 | Wright et al. |
| 2013/0226026 A1 | 8/2013 | Dillard et al. |
| 2013/0245732 A1 | 9/2013 | Jarl et al. |
| 2014/0031843 A1 | 1/2014 | Rottenberg et al. |
| 2014/0148759 A1 | 5/2014 | Macnamara et al. |
| 2014/0246407 A1 | 9/2014 | Simpson et al. |
| 2014/0276642 A1 | 9/2014 | Cully et al. |
| 2014/0276966 A1 | 9/2014 | Ranucci et al. |
| 2014/0350462 A1 | 11/2014 | Ataollahi et al. |
| 2014/0378868 A1 | 12/2014 | Griego et al. |
| 2015/0066128 A1 | 3/2015 | Losordo et al. |
| 2015/0066129 A1 | 3/2015 | Nageswaran et al. |
| 2015/0066131 A1 | 3/2015 | Luong et al. |
| 2015/0099997 A1 | 4/2015 | Cabiri |
| 2015/0119754 A1 | 4/2015 | Ostrovski et al. |
| 2015/0164542 A1 | 6/2015 | Wulfman et al. |
| 2015/0238336 A1 | 8/2015 | Johnson et al. |
| 2015/0250981 A1 | 9/2015 | Beasley et al. |
| 2016/0206860 A1 | 7/2016 | Gupta |
| 2016/0310702 A1 | 10/2016 | Cabiri |
| 2017/0035592 A1 | 2/2017 | Haggstrom et al. |
| 2017/0173303 A1 | 6/2017 | Salahieh et al. |
| 2017/0189645 A9 | 7/2017 | Cully et al. |
| 2021/0330310 A1 | 10/2021 | Giles |
| 2022/0023593 A1 | 1/2022 | Giles |

FOREIGN PATENT DOCUMENTS

| | | |
|---|---|---|
| JP | 2015-192845 | 11/2015 |
| WO | WO 1999/051140 | 10/1999 |
| WO | WO 2000/033984 | 6/2000 |
| WO | WO 2005/105191 | 11/2005 |
| WO | WO 2017/037538 | 3/2017 |

OTHER PUBLICATIONS

Dong et al., Dual-Chirality Helical Nanobelts: Linear-to-Rotary Motion Converters for Three-Dimensional Microscopy, Journal of Microelectromechanical Systems, vol. 18, No. 5, Oct. 2009.

International Search Report for related PCT App. No. PCT/US2017/41224, dated Nov. 16, 2017.

Extended European Search Report dated Feb. 4, 2020 for European Patent Office Appl. No. 17825038.7, which is in the same patent family as the present application.

U.S. Appl. No. 15/204,800 (U.S. Pat. No. 10,391,274), Jul. 7, 2016, Medical Device With Distal Torque Control.

U.S. Appl. No. 15/660,811 (U.S. Pat. No. 9,918,705), Jul. 26, 2017, Medical Devices With Distal Control.

U.S. Appl. No. 15/924,027 (U.S. Pat. No. 10,786,230), Mar. 16, 2018, Medical Devices With Distal Control.

U.S. Appl. No. 16/192,755 (U.S. Pat. No. 11,141,141), Nov. 15, 2018, Medical Devices With Distal Control.

U.S. Appl. No. 17/498,701, filed Oct. 11, 2021, Medical Devices With Distal Control.

U.S. Appl. No. 17/370,986, filed Jul. 8, 2021, Medical Devices With Distal Control.

\* cited by examiner

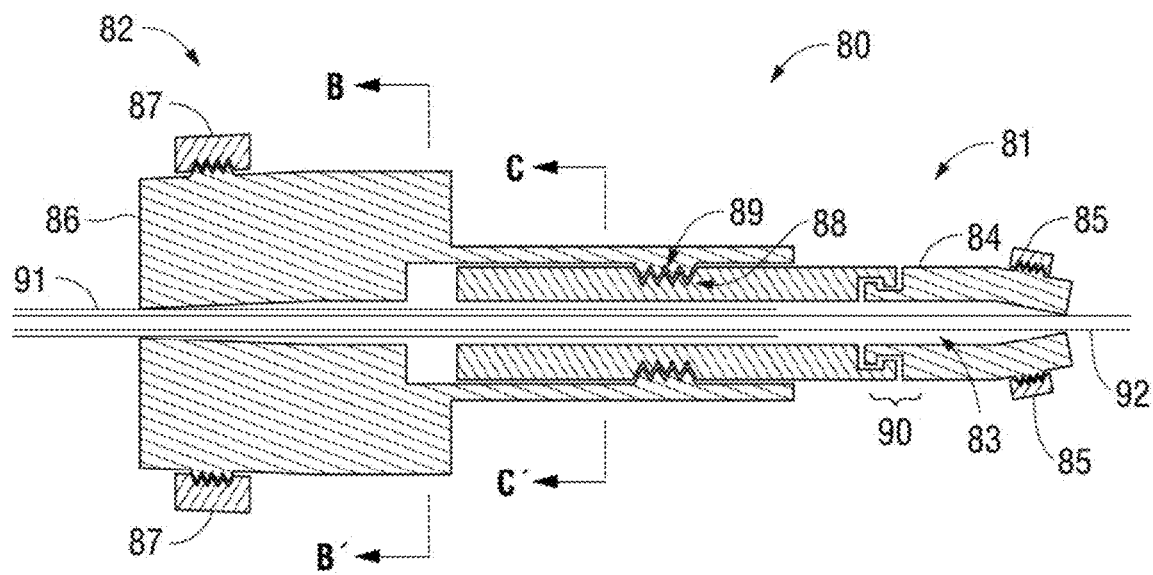
FIG. 15A
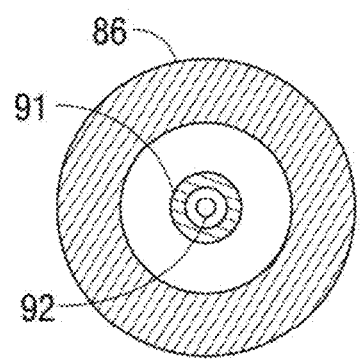 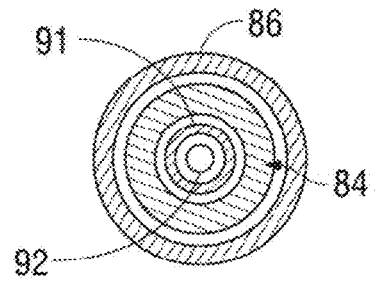
FIG. 15B          FIG. 15C

FIG. 21B FIG. 21C

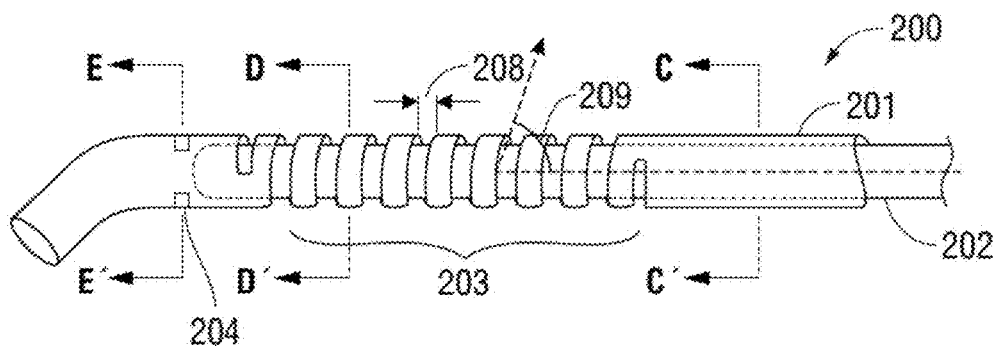
FIG. 23A
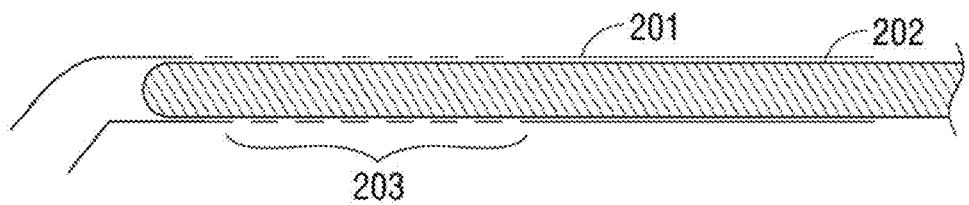
FIG. 23B
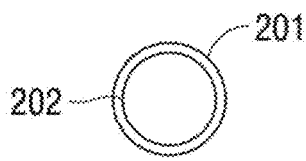   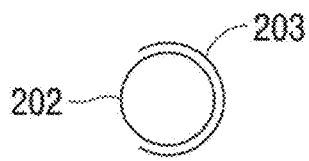   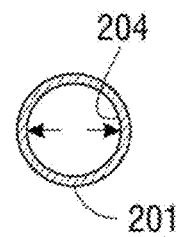
FIG. 23C          FIG. 23D          FIG. 23E
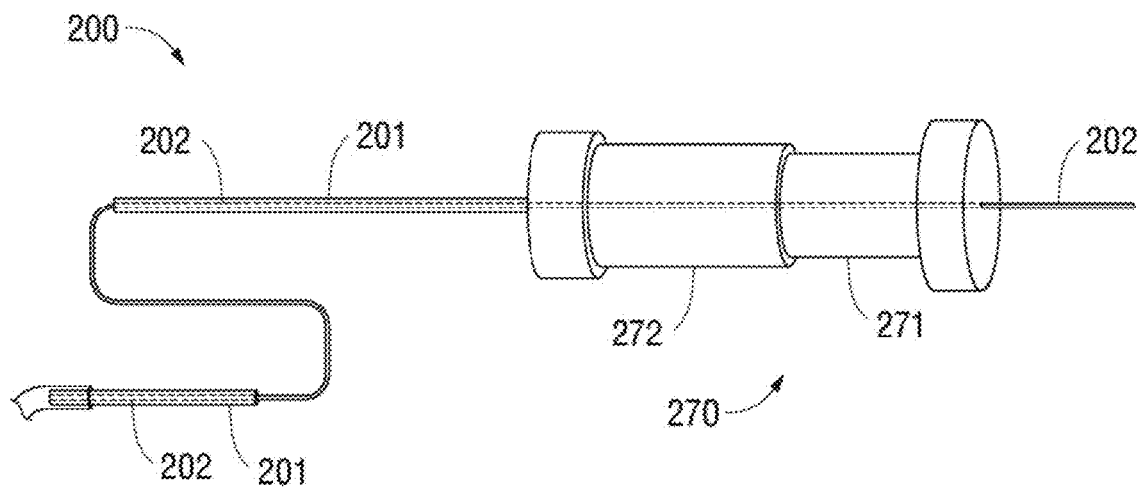
FIG. 23F

MEDICAL DEVICE WITH DISTAL TORQUE CONTROL

CROSS-REFERENCE TO RELATED APPLICATIONS

This application is a continuation of U.S. patent application Ser. No. 15/204,800, filed Jul. 7, 2016. The entirety of the aforementioned application is hereby incorporated by reference herein.

BACKGROUND

Field

The disclosure is in the general field of surgical instruments and relates specifically to catheters, guidewires, endoscopes and endoscopic devices that are used in minimally invasive procedures, such as cardiovascular and endovascular procedures to facilitate the placement of devices within endoluminal structures within the body, such as, but not limited to, blood vessels, the gastrointestinal tract and the genitourinary tract.

Description of the Related Art

Catheters, guidewires, endoscopes and associated endoscopic instruments have been used to diagnose and treat conditions by accessing luminal structures of the body. Luminal structures of the body may include, but are not limited to, blood vessels, the heart, the gastrointestinal (GI) tract, genitourinary (GU) tract, peritoneal cavity, thoracic cavity, the mediastinum, bronchial passages, subarachnoidal spaces, and the intracranial ventricular system. Catheters, guidewires, and endoscopes may be used in laparoscopic surgeries and other procedures where invasiveness is to be minimized. These devices are manipulated by transmitting forces from the proximal end (i.e. the end of the device external to the body) to the distal end (i.e. the end of the device within the body) along and through the longitudinal structure of the device. Precise control of the distal portion of the device is required for medical procedures, so as to precisely cannulate the desired luminal structure, such as a blood vessel. In order to achieve this, multiple design criteria must be considered during the design process of endoluminal devices, such as a guidewires and catheters. Major design criteria include push-ability, torque-ability, and flexibility.

Push-ability refers to the ability to move the device along the longitudinal axis of the device, resulting in translational motion. Push-ability is directly dependent on the stiffness of the device, which is largely dependent on the modulus of elasticity of the material employed within the device. Devices with a high modulus of elasticity are able to transmit force along the length of the device effectively, while devices with a low modulus of elasticity do not transmit force along the device as effectively, resulting in deformation or buckling of the device.

Torque-ability refers to the ability of rotational motion to be transmitted along the length of the device and is directly dependent on the modulus of rigidity (or shear modulus) of the material employed within the device. Devices having a high modulus of rigidity are able to transmit torque along the length of the device effectively, while devices having a low modulus of rigidity do not transmit force along the device as effectively.

Flexibility refers to the ability of a device to bend and flex along its lateral axis. Flexibility is necessary to enable the device to follow the bends and turns that are present in the human vasculature. Flexibility may be affected by the type of material and/or structural factors, such as the spacing and size of slits in the device that allow bending. However, flexibility is inversely dependent to the modulus of elasticity and modulus of rigidity and thus comes at the expense of push-ability and torque-ability.

Ideally a device, such as a catheter, guidewire, endoscope or endoscopic instrument, will demonstrate one-to-one rotation of the distal end with respect to the proximal end. For example, if the proximal end of a device is rotated 90 degrees clockwise, the distal end of the device will also rotate 90 degrees clockwise. Unfortunately, in practice this does not typically occur, especially when the device has one or more bends or loops along its length secondary to the tortuous path of the bodily luminal structures. The inherent tortuosity of bodily structures (blood vessels, GI and GU tracts) means that portions of the device are subjected to frictional forces as the device is maneuvered within the body.

These frictional forces can impede the transmission of forces from the proximal end to the distal end of a device. One particularly problematic area is torque transmission along a device. As a result, potential energy is oftentimes stored along the length of the device as the proximal end is rotated. As this stored up potential energy within the device overcomes the frictional forces that are being exerted along the device, a sudden rotation of the device when the potential energy is released, also known as "device whip," can occur. This can make cannulating a desired vessel difficult and may cause injury to the patient. Thus, current devices, such as catheters, guidewires endoscopes and endoscopic instruments, strive for a balance between stiffness and flexibility in a variety of ways.

Devices with Improved Torque Transmission.

For most guidewires, catheters, endoscopes and endoscopic devices an operator turns the proximal end of the device in order to turn the distal end of the device. By turning the proximal end of the device torque is transmitted down the length of the device to the distal end. However, given frictional forces that occur between the device and the bodily lumen, the degree of rotation on the proximal end does not equate to the degree of rotation on the distal end secondary to the shaft of the device undergoing torsional strain. In order to overcome this difference in rotation between the proximal and distal ends, various improvements in the design of the shaft the device have been proposed.

U.S. Patent application 20150250250981 discloses a device that has one or more cuts that enhance flexibility without compromising axial or torsional stiffness and has a shaft with the capability to distally transfer rotational motion from the proximal end to the distal end. The device is shown in one embodiment with a helically wound elongated member having a series of windings with different average helix angles and opposite chirality on either side of a transition region. However, the shaft is still subject to torsional strain along its length and thus does not have the ability to reliably rotate the proximal end and obtain accurate rotation of the distal end of the device. There is also no teaching of converting linear motion to rotational motion.

U.S. Patent Publication 20060100687 discloses a device with spiral slots cut into the side wall of a hypotube to increase flexibility of said hypotube and the slots are interrupted by solid strut. The struts are proposed to prevent elongation of the device. However, the shaft is still subject to torsional strain along its length and thus does not have the ability to reliably rotate the proximal end and obtain accurate rotation of the distal end of the device. There is also no teaching of converting linear motion to rotational motion.

U.S. Pat. No. 7,763,012 discloses a device with a first helical coil nested within the second helical coil and wound in a reverse direction from the second helical coil so that rotation of the first helical coil in a first direction causes the first helical coil to expand while rotation of the second helical coil in the first direction causes the second helical coil to compress and thereby interfere with the expansion of the first helical coil. It is proposed that nested helical coils maximize the torque transmission properties of the device. However, the shaft is still subject to torsional strain along its length and thus does not have the ability to reliably rotate the proximal end and obtain accurate rotation of the distal end of the device. There is also no teaching of converting linear motion to rotational motion.

U.S. Patent Publication 20090306587 discloses a sleeve steering device and reinforcement for a tip deflectable catheter with at least two helical wound elements. The helical wound elements are wound in different directions and provided to facilitate torque transmission along the device. However, the shaft is still subject to torsional strain along its length and thus does not have the ability to reliably rotate the proximal end and obtain accurate rotation of the distal end of the device. There is also no teaching of converting linear motion to rotational motion.

U.S. Pat. No. 6,890,329 discloses a defined deflection structure a tip deflecting catheter where the defined deflection structure provides a deflection mechanism capable of deflecting portions of a flexible body in more than one direction, allowing the distal portion of a catheter to be deflected more than 360 degrees to provide a loop. However, the shaft is still subject to torsional strain along its length and thus does not have the ability to reliably rotate the proximal end and obtain accurate rotation of the distal end of the device. There is also no teaching of converting linear motion to rotational motion.

U.S. Pat. No. 6,022,343 discloses a bridged coil catheter support structure for a catheter where adjacent turns of a helical coil are joined by bridging members. The bridging members add kink resistance and enhance one-to-one push responsiveness and prevent stretching during pull-back. However, the shaft is still subject to torsional strain along its length and thus does not have the ability to reliably rotate the proximal end and obtain accurate rotation of the distal end of the device. There is also no teaching of converting linear motion to rotational motion.

U.S. Patent Publication 20130245732 discloses a lead header and manufacture thereof for implantation of cardiac leads. The lead head provides a helical fixation element that converts rotational motion to linear motion for the implantation of cardiac leads. However, the shaft is still subject to torsional strain along its length and thus does not have the ability to reliably rotate the proximal end and obtain accurate rotation of the distal end of the device. There is also no teaching of converting linear motion to rotational motion.

WO199951140 discloses a cannula of changeable length and shape. The cannula includes one or more spirally wound bands in which the place(s) of overlapping are linked by magnetic or other forces and where the free unlinked sections of the bands in the cannula walls are located freely in the channels so that rotation in one direction results in lengthening of the cannula while rotation in the opposite direction results in shortening. However, the shaft is still subject to torsional strain along its length and thus does not have the ability to reliably rotate the proximal end and obtain accurate rotation of the distal end of the device. There is also no teaching of converting linear motion to rotational motion.

U.S. Pat. No. 8,366,699 discloses a double helix reinforced catheter for improvement in critical mechanical properties such as torque, kink resistance, axial rigidity and distal compliance. The catheter provides a double helical coil geometry that transitions into a single helical coil at a specific point along the axis. However, the shaft is still subject to torsional strain along its length and thus does not have the ability to reliably rotate the proximal end and obtain accurate rotation of the distal end of the device. There is also no teaching of converting linear motion to rotational motion.

U.S. Pat. No. 8,425,532 discloses a method and apparatus for accessing the interior of a hip joint, including a telescoping access cannula and a telescoping obturator. The disclosure provides a rotatable member carried by the outer tube and connected to the inner tube, wherein rotation of the rotatable member causes longitudinal movement of the inner tube relative to the outer tube. However, the shaft is still subject to torsional strain along its length and thus does not have the ability to reliably rotate the proximal end and obtain accurate rotation of the distal end of the device. There is also no teaching of converting linear motion to rotational motion.

U.S. Pat. No. 4,321,931 discloses an electrode structure and applicator therefor with a tooth and rib mechanism that converts rotational motion to linear motion for the implantation of fetal scalp electrode. However, the shaft is still subject to torsional strain along its length and thus does not have the ability to reliably rotate the proximal end and obtain accurate rotation of the distal end of the device. There is also no teaching of converting linear motion to rotational motion.

Becton, Dickenson and Company (BD) manufactures the SPIROL® line of spring-reinforced epidural catheters where the catheter is comprised of a spring coil with variable softness and firmness in the body. However, the shaft is still subject to torsional strain along its length and thus does not have the ability to reliably rotate the proximal end and obtain accurate rotation of the distal end of the device. There is also no teaching of converting linear motion to rotation motion.

Devices with Conversion of Linear to Rotational Motion.

U.S. Pat. No. 5,269,757 to Fagan et al. discloses a catheter with an integral steerable guidewire having linear to rotary movement. The catheter and guidewire have cooperative elements that are engageable with one another whereby the cooperative elements are nonlinear helical portions of the catheter and guidewire. Shortcomings of the '757 patent's approach include 1) the use of a nonlinear helical portion can result in difficulty in advancing this portion of the catheter beyond tortuous vasculature, 2) the nonlinear helical portion can lead to a higher susceptibility to buckling of the catheter and guidewire at this location when attempting to advance the catheter or guidewire through tortuous anatomy, and 3) the cross sectional length of the flat twisted portion of the guidewire is greater than the cross sectional diameter of the guidewire either proximal or distal to the flat twisted portion, resulting in the need for a greater outer diameter of the catheter which in turn limits the ability to catheterize small blood vessels.

U.S. Pat. No. 6,602,262 discloses a medical device that converts linear movement of a shaft at the proximal end to rotational movement at the effector end of the medical device. The shaft is formed with a threaded portion that matches the threads formed in a torque transmitter disposed within the sleeve. The part of the inner surface of the sleeve has undulations. The threaded shaft and sleeve with undulations along the inner surface would result in an overall increase in the outer diameter of the device. A shortcoming of this device is that the guidewire cannot be advanced or withdrawn with respect to the catheter without resultant rotational motion of the distal end of the guidewire. Thus, linear displacement of the catheter as a whole cannot be achieved independent of rotation of the distal end. This is problematic since different bodies, and even different luminal spaces within the same body, need different lengths of guidewire extending from the distal end of the catheter. For example for one individual the guidewire may optimally need to extend 1 cm from the distal end of the catheter in order to select the desired branch; however, either for another branch within the same individual or for a different individual the guidewire may optimally need to extend 2 cm from the distal end of the catheter in order to select the desired branch. Moreover, given the small sizes (e.g., 0.014"-0.038") of commonly used guidewires, manufacturing the above sleeve disclosed in the '262 patent with undulations along part of the inner surface and the threads on the shaft would have to be manufactured with tight tolerances, which in turn would result in significant manufacturing costs.

U.S. Patent Publication 20100114151 discloses a device for deployment into a lumen for implantation of occlusion devices for contraceptive purposes. A tooth and groove mechanism (cam path), rack and pinion or spring loaded handle mechanisms for the conversion of linear motion of the handle to rotational motion of the handle are provided to rotate the catheter. A shortcoming of this approach is that the element within the lumen of catheter (in this case the occlusion device) cannot be advanced or withdrawn with respect to the catheter independent of rotational motion of the distal end of the element within the lumen of catheter. Thus, the catheter would need to continuously rotate while the catheter and its guidewire are navigated within the body. Further, the conversion of linear motion to rotational motion does not use a member coupled to a dual chirality helix or a single helix.

A need exists for a method and apparatus for imparting precise, reliable rotational motion to the distal aspect of a medical device that has a compact profile and allows for individual components to be manipulated independently of one another, such as catheter and guidewire.

SUMMARY

The present disclosure is directed to a method and apparatus with rotation of the distal end of a medical device, such as a catheter, guidewire, chronic total occlusion crossing device, endoscope or endoscopic instrument, specifically, a medical device with a dual chirality helix converting linear movement into rotational movement at the distal end.

One embodiment according to the present disclosure includes a medical device comprising: a tubular member with a longitudinal axis having a distal end and a proximal end comprising: a distal aspect terminating at the distal end with a distal helix formed by distal helical cut terminating at the proximal side of the distal aspect; a proximal aspect terminating at the proximal end with a proximal helix formed by proximal helical cut terminating at the distal side of the proximal aspect, wherein the proximal helical cut is one of right or left handed and the distal helical cut is the other of right and left handed; and a junction where the distal aspect and the proximal aspect are joined; a longitudinal displacer disposed within the tubular member and slidable relative to the tubular member; and a distal segment disposed around part of the tubular member and coupled to the tubular member at the junction. The distal helical cut has a distal helical cut width and the proximal helical cut has a proximal helical cut width and the distal helical cut width may be equal to or different from the proximal helical cut width and each of the helical cuts may range between about 0.1 micrometers to about 30 millimeters. The helical cuts each have helical cut angles which may be same or different in magnitude and may range from about 10 to about 80 degrees. The tubular member may be made of one or more of: polyimide, polyurethane, polyether block amide, nylon, nickel titanium, stainless steel braiding, and hollow helical stranded tubing or other suitable material that would be understood by a person of ordinary skill in the art. The coupling means may include: 1) adhesive, 2) welding, 3) brazing, 4) soldering, 5) mechanical linking, or other suitable means understood by a person of ordinary skill in the art. The longitudinal displacer may include a longitudinal member with an outer diameter. The tubular member has inner diameter such that the inner diameter of the tubular member is greater than the outer diameter of the longitudinal member except for a portion between the distal end of the distal aspect and the junction where the inner diameter of the tubular member is reduced to less than the outer diameter of the longitudinal member such that longitudinal movement of the longitudinal member toward the distal end of the tubular member imparts longitudinal force on the distal aspect. The medical device may include a cap disposed on the distal end of the tubular member obstructing forward movement of the longitudinal displacer. The longitudinal displacer comprises a membrane configured to elongate when fluid is injected and longitudinally displace the distal end of the dual chirality helix. The medical device may include a first magnetic element disposed on the distal aspect of the tubular member; a second magnetic element disposed on the proximal aspect of the tubular member; and a power source configured to energize at least one of the first and second magnetic elements. The distal and proximal helices are comprised of at least one of: a shape memory alloy and a shape memory polymer. The first magnetic element may be one of: a magnet, an electret, a wire, and a coil configured to carry current and generate a magnetic field, and the second magnetic element may be one of: a magnet, a ferromagnetic material, an electret, a wire, and a coil configured to carry current and generate a magnetic field.

Another embodiment according to the present disclosure is a medical device including: a tubular member with a longitudinal axis having a distal end and a proximal end including: a distal aspect terminating at the distal end with a helix formed by a helical cut terminating at the proximal side of the distal aspect; and a proximal aspect terminating at the proximal end; and a longitudinal displacer disposed within the tubular member and slidable relative to the tubular member and configured to impart longitudinal force on the distal helix. The distal cut width may be in a range of about 0.1 micrometers to about 30 millimeters, and the distal helical cut angle may be between about 10 and about 80 degrees. The tubular member may be made of one or more of: polyimide, polyurethane, polyether block amide, nylon, nickel titanium, stainless steel braiding, and hollow helical stranded tubing and wherein the coupling means comprises at least one of: 1) adhesive, 2) welding, 3) brazing, 4) soldering, and 5) mechanical linking. The longitudinal displacer may include a longitudinal member with an outer diameter, and the tubular member has inner diameter such that the inner diameter of the tubular member is greater than the outer diameter of the longitudinal member except for a portion between the distal end of the distal aspect and the junction where the inner diameter of the tubular member is reduced to less than the outer diameter of the longitudinal member such that longitudinal movement of the longitudinal member toward the distal end of the tubular member imparts longitudinal force on the distal aspect. The medical device may also include a cap disposed on the distal end of the tubular member obstructing forward movement of the longitudinal displacer. The longitudinal displacer may include a membrane configured to elongate when fluid is injected and longitudinally displace the distal end of the helical cut tubing. The distal helix may include at least one of: a shape memory alloy and a shape memory polymer; and further comprising: a first magnetic element disposed on one of the distal aspect and the proximal aspect of the tubular member; a second magnetic element disposed on the other of the distal aspect and the proximal of the tubular member; and a power source configured to energize at least one of the first and second magnetic elements; wherein the first magnetic element is one of: a magnet, an electret, a wire, and a coil configured to carrying current and generate a magnetic field; and wherein the second magnetic element is one of: a magnet, a ferromagnetic material, an electret, a wire, and a coil configured to carrying current and generate a magnetic field.

Another embodiment according to the present disclosure is a method for controlling the distal end of the a medical device that includes a tubular member with a longitudinal axis having a distal end and a proximal end comprising: a distal aspect terminating at the distal end with a distal helix formed by distal helical cut terminating at the proximal side of the distal aspect; a proximal aspect terminating at the proximal end with a proximal helix formed by proximal helical cut terminating at the distal side of the proximal aspect, wherein the proximal helical cut is one of right or left handed and the distal helical cut is the other of right and left handed; and a junction where the distal aspect and the proximal aspect are joined; a longitudinal displacer disposed within the tubular member and slidable relative to the tubular member; and a distal segment disposed around part of the tubular member and coupled to the tubular member at the junction. The method includes inserting the medical device into an endoluminal structure of a body; displaying an image of the medical device within the body; selecting a region of interest within the image; applying longitudinal force to displace the dual chirality helix causing rotation of the distal end; observing the change in position of the distal end on the display; and adjusting the amount of longitudinal displacement is adjusted to rotate the distal end the desired degree of rotation. The display may be in form of any imaging techniques for objects internal to the human body, including, but not limited to, x-ray fluoroscopy, ultrasound imaging, computed axial tomography (CAT) imaging, magnetic resonance imaging (MRI), and/or endoscopic imaging.

Another embodiment according to the present disclosure is a device including a tube with a distal end and a proximal end wherein a dual chirality helix is cut into the distal aspect of the tube, a wire, a slidable sleeve located coaxially over the wire, a distal segment that is coupled to the junction of the two helices of the dual chirality helix and a handle with controlled linear displacement. By its nature, the junction of the left and right handed helices rotates when the ends of the dual chirality helix are linearly extended or retracted, resulting in the conversion of linear movement to rotational motion of the junction point of the two helices. The distal segment is located circumferentially around the distal aspect of the tube in which the dual chirality helix is inscribed. The distal segment is coupled to the junction of the helices of the dual chirality helix. The tip of the distal segment can have an angulated tip so as to aid in improved navigation of the device. The tube has a shelf of a reduced luminal inner diameter distal to the dual chirality helix. The outer diameter of the sleeve is greater than the inner diameter of the shelf of the tube, but is less than the inner diameter of the tube proximal to said shelf. The sleeve slidably abuts and engages said shelf of the tube. Advancing the sleeve results in linear displacement of the dual chirality helix. The handle with controlled linear displacement enables controlled movement of the sleeve with respect to the long axis of the tube. This in turn results in rotation of the junction point of the left and right handed helices and subsequent rotation of the distal segment. The degree of rotation is proportional to the linear displacement of the dual chirality helix of the tube.

Another embodiment according to the present disclosure is a device including a tube with a distal end and a proximal end wherein a dual chirality helix is cut into the distal aspect of the tube, a wire with a tapered distal end, a distal segment that is coupled to the junction of the two helices of the dual chirality helix and a handle with controlled linear displacement. By its nature, the junction of the left and right handed helices rotates when the ends of the dual chirality helix are linearly extended or retracted, resulting in the conversion of linear movement to rotational motion of the junction point of the two helices. The distal segment is located circumferentially around the distal aspect of the tube in which the dual chirality helix is inscribed. The distal segment is coupled to the junction of the helices of the dual chirality helix. The tip of the distal segment can have an angulated tip so as to aid in improved navigation of the device. The tube has a shelf of a reduced luminal inner diameter distal to the dual chirality helix. The diameter of the tapered portion of the wire is less than the inner diameter of the shelf. The outer diameter of the non-tapered portion of the wire is greater than the inner diameter of the shelf of the tube, but is less than the inner diameter of the tube proximal to said shelf. The non-tapered portion of the wire abuts and engages said shelf of the tube. Advancing the wire results in linear displacement of the dual chirality helix. The handle with controlled linear displacement enables controlled movement of the wire with respect to the long axis of the tube. This in turn results in rotation of the junction point of the left and right handed helices and subsequent rotation of the distal segment. The degree of rotation is proportional to the linear displacement of the dual chirality helix of the tube.

Another embodiment according to the present disclosure is a device including a tube with a distal end and a proximal end wherein a dual chirality helix is cut into the distal aspect of the tube, a wire with a reversibly expandable member, a distal segment that is coupled to the junction of the two helices of the dual chirality helix and a handle with controlled linear displacement. The wire slidably engages the lumen of the tube. A reversibly expandable member is located along the distal aspect of the wire. By its nature, the junction of the left and right handed helices rotates when the ends of the dual chirality helix are linearly extended or retracted, resulting in the conversion of linear movement to rotational motion of the junction point of the two helices. The distal segment is located circumferentially around the distal end of the tube and is coupled to the junction of the left and right handed helices of the dual chirality helix. The tip of the distal segment can have an angulated tip so as better select branch vessels. With the expandable member collapsed, the outer diameter of the wire is less than the inner diameter of the hypotube and thus the wire is able to free move within the lumen of the tube. However, the outer diameter of the expandable member in its expanded state is greater than the inner diameter of the tube. When the reversibly expandable member is expanded, it engages the distal end of the tube. Subsequent advancement of the wire then results in linear displacement of the dual chirality helix. The handle with controlled linear displacement enables controlled movement of the wire with respect to the long axis of the tube. This in turn results in rotation of the junction point of the left and right handed helices and subsequent rotation of the distal segment. The degree of rotation is proportional to the linear displacement of the dual chirality helix of the tube.

Another embodiment according to the present disclosure is a device including a tube with a distal end and a proximal end wherein a dual chirality helix is cut into the distal aspect of the tube and wherein the distal end is capped, a wire, a distal segment that is coupled to the junction of the two helices of the dual chirality helix and a handle with controlled linear displacement. By its nature, the junction of the left and right handed helices rotates when the ends of the dual chirality helix are linearly extended or retracted, resulting in the conversion of linear movement to rotational motion of the junction point of the two helices. The distal segment is located circumferentially around the distal aspect of the tube in which the dual chirality helix is inscribed. The distal segment is coupled to the junction of the helices of the dual chirality helix. The tip of the distal segment can have an angulated tip so as to aid in improved navigation of the device. The outer diameter of the wire is less than the inner diameter of the tube. The distal end of the wire abuts and engages the capped distal end of the tube. Advancing the wire results in linear displacement of the dual chirality helix. The handle with controlled linear displacement enables controlled movement of the wire with respect to the long axis of the tube. This in turn results in rotation of the junction point of the left and right handed helices and subsequent rotation of the distal segment. The degree of rotation is proportional to the linear displacement of the dual chirality helix of the tube.

Another embodiment according to the present disclosure is a device including a tube with a distal end and a proximal end wherein a dual chirality helix is cut into the distal aspect of the tube and wherein the distal end is capped, a liner that encompasses the dual chirality helix, a distal segment that is coupled to the junction of the two helices of the dual chirality helix and a handle with controlled linear displacement. By its nature, the junction of the left and right handed helices rotates when the ends of the dual chirality helix are linearly extended or retracted, resulting in the conversion of linear movement to rotational motion of the junction point of the two helices. The distal segment is located circumferentially around the distal aspect of the tube in which the dual chirality helix is inscribed. The distal segment is coupled to the junction of the helices of the dual chirality helix. The tip of the distal segment can have an angulated tip so as to aid in improved navigation of the device. Injecting fluid into the lumen of the tube results in varying degrees of linear displacement of the dual chirality helix. This in turn results in rotation of the junction point of the left and right handed helices and subsequent rotation of the distal segment. The degree of rotation is proportional to the linear displacement of the dual chirality helix of the tube.

A handle can be applied to the proximal end of the sleeve or wire and the proximal end of the tube in order to provide more precise movement of the sleeve or wire with respect to elongated tube. This handle can be comprised of two coaxial tubes that capable of displacement with respect to one another along the long axis of the tubes. Means for translational motion with respect to one another include but are not limited to 1) manual displacement of the two coaxial tubes along the long axis of the tubes; 2) threaded portions of each tubes that are coaxially receivable such that rotation of the tubes along the threaded portions results in linear displacement of the tubes with respect to one another (similar mechanism to the linear movement of screwing a bolt into a nut.) The handle is able to coaxially receive the inner wire and elongated tube within the lumen of the gripper device. Fastening mechanisms can be located along each end of the handle so as to grip the sleeve or wire at one end and the tube at the other end. These fastening mechanisms can be permanently or reversibly fixed in place. These fastening mechanisms can also swivel about the sleeve or wire or elongated tube such the sleeve, wire or elongated tube do not undergo rotational motion while one or more of the coaxial tubes are being rotated.

Another embodiment according to the present disclosure is a device including a tube with a distal end and a proximal end wherein a dual chirality helix is cut into the distal aspect of the tube and wherein said elongated tube is comprised of material capable of undergoing a shape transformation in response to a change in the surrounding environment, a distal segment that is coupled to the junction of the two helices of the dual chirality helix, a means for causing the tube to undergo shape transformation and a means for counteracting the shape transformation of the tube. By its nature, the junction of the left and right handed helices rotates when the ends of the dual chirality helix are linearly extended or retracted, resulting in the conversion of linear movement to rotational motion of the junction point of the two helices. The distal segment is located circumferentially around the distal end of the tube and is coupled to the junction of the left and right handed helices of the dual chirality helix. The tip of the distal segment can have an angulated tip so as better select branch vessels. Alterations in environment including but not limited to temperature, electric field, pH, light, ion concentration result in shape transformation of the tube such that there is linear displacement of the dual chirality helix. This in turn results in rotation of the junction point of the left and right handed helices and subsequent rotation of the distal segment. The degree of rotation is proportional to the linear displacement of the dual chirality helix of the tube. A means for counteracting the shape transformation of the tube, including but not limited to coupling the conduit to the distal end of the tube. Varying amounts of tension can be applied to the conduit in order to counteract the linear displacement of the dual chirality helix.

Another embodiment according to the present disclosure is a device including a tube with a distal end and a proximal end wherein a dual chirality helix is cut into the distal aspect of the tube, a distal segment that is coupled to the junction of the two helices of the dual chirality helix, a means for linear displacement of the tube containing dual chirality cut wherein said means includes but is not limited to repulsion of electrical fields or repulsion of magnetic fields. By its nature, the junction of the left and right handed helices rotates when the ends of the dual chirality helix are linearly extended or retracted, resulting in the conversion of linear movement to rotational motion of the junction point of the two helices. The distal segment is located circumferentially around the distal end of the tube and is coupled to the junction of the left and right handed helices of the dual chirality helix. The tip of the distal segment can have an angulated tip so as better select branch vessels. Examples of means for applying opposing electrical or magnetic fields along or proximate to the region of the dual chirality helix include but are not limited to 1) applying a permanent electrical or magnetic charge on one end of the dual chirality helix and a variable, inducible charge on the opposite end of the dual chirality helix; 2) applying an inducible electrical or magnetic charge on one end of the dual chirality helix and a variable, inducible electrical or magnetic charge on the opposite end of the dual chirality helix; 3) applying an electrical or magnetic charge on one end of the dual chirality helix cut and an electrical or magnetic charge on a portion of guidewire proximate to the dual chirality helix. The opposing electrical or magnetic forces results in linear displacement of the dual chirality helix. This in turn results in rotation of the junction point of the left and right handed helices and subsequent rotation of the distal segment. The degree of rotation is proportional to the linear displacement of the dual chirality helix of the tube.

Another embodiment according to the present disclosure is a device including a tube with a distal end and a proximal end, a wire with two or more outer diameters, and a means for advancing the wire. A dual chirality helix is cut into the tube just proximal to the reduced luminal inner diameter of the tube. By its nature, the junction of the left and right handed helices rotates when the ends of the dual chirality helix are linearly extended or retracted, resulting in the conversion of linear movement to rotational motion of the junction point of the two helices. A means for engaging the wire, including but not limited to a tooth, is present on the junction point of the left and right handed helices. One or more grooves are located along the longitudinal axis of the wire along the tapered portion of the wire and the grooves extend slightly proximal to the transition the diameter of the wire. The tooth slidably engages one or more grooves along the distal aspect of the inner wire. The diameter of the distal aspect of the wire is less than the proximal diameter. The luminal inner diameter of the distal end of the tube is greater than the diameter of the distal aspect of the wire and less than the diameter of the proximal aspect of the wire. Advancing the wire into the tube results in linear displacement of the dual chirality helix. This in turn results in rotation of the junction point of the left and right handed helices and subsequent rotation of the distal aspect of the wire. The degree of rotation is proportional to the linear displacement of the dual chirality helix of the tube.

BRIEF DESCRIPTION OF THE DRAWINGS

For a detailed understanding of the present disclosure, reference should be made to the following detailed description of the embodiments, taken in conjunction with the accompanying drawings, in which like elements have been given like numerals, wherein:

FIG. 15A is a longitudinal cross sectional view of the handle with controlled linear displacement in a closed state;

FIG. 15B is a transverse cross sectional view of the handle with controlled linear displacement through B-B' in FIG. 15A.

FIG. 15C is a transverse cross sectional view of the handle with controlled linear displacement through C-C' in FIG. 15A.

FIG. 21B is a transverse cross sectional view of the distal aspect of the medical device in FIG. 21A through B-B' with no force applied to the distal end of the dual chirality helix;

FIG. 21C is a transverse cross sectional view of the distal aspect of the medical device in FIG. 21A through C-C' with no force applied to the distal end of the dual chirality helix;

FIG. 23A is a diagram of a catheter with a single helix formed from a tube according to one embodiment of the present disclosure;

FIG. 23B is a cross-sectional view of FIG. 23A;

FIG. 23C is a transverse cross section of FIG. 23A through lines C-C';

FIG. 23D is a transverse cross section of FIG. 23A through lines D-D';

FIG. 23E is a transverse cross section of FIG. 23A through lines E-E';

FIG. 23F is a diagram of a handle connected to the catheter of FIG. 23A;

All figures are drawn for ease of explanation of the basic teachings of the present invention only; the extensions of the figures with respect to number, position, relationship, and dimensions of the parts to form the preferred embodiment will be explained or will be within the skill of the art after the following teachings of the present invention have been read and understood. Further, the exact dimensions and dimensional proportions to conform to specific force, weight, strength, and similar requirements will likewise be within the skill of the art after the following teachings of the present invention have been read and understood.

DETAILED DESCRIPTION

The present disclosure is directed to a medical device comprised of a distal portion, a proximal portion and a helical structure incorporated into the distal end of the device so as to convert linear motion to rotational motion at the distal end of the device, such as a catheter. The helical structure may be a single helix or a dual chirality helix. A dual chirality helix is comprised of a helix with a clockwise rotation and a helix with a counterclockwise rotation wherein the two helices intersect with one another. Displacement of the dual chirality helix along its long axis results in rotation of the junction of the two helices. While the medical device has application in human surgical and diagnostic procedures, the present disclosure contemplates the device having application and use in human and non-human medical procedures, as well as, non-medical applications for industrial and diagnostic procedures, such as inspections.

Imparting rotation on the distal portion at the distal end, as opposed to rotating the entire length of the medical device, reduces that stress on the vasculature, improves the accuracy of the rotation of the medical device, and reduces the risk of uncontrolled release of potential energy from the medical device. These qualities enable the medical device to improve surgical efficiency, reduce overall time for the patient in the operating theater, reduces the time that the patient is required to be exposed to anesthesia, reduces the risk of surgical complications, reduces fatigue of the surgical staff during a medical procedure, and reduces the exposure time of the patient to radiation, when a radiation source is required during the operation.

The terms "top," "bottom," "first," "second," "upper," "lower," "height," "width," "length," "end," "side," "horizontal," "vertical," and similar terms are used herein, it should be understood that these terms have reference only to the structures shown in the figures and are utilized only to facilitate describing embodiments of the disclosure. Features depicted some embodiments may be used in other embodiments disclosed herein as would be understood by a person of ordinary skill in the art.

Figure 1:
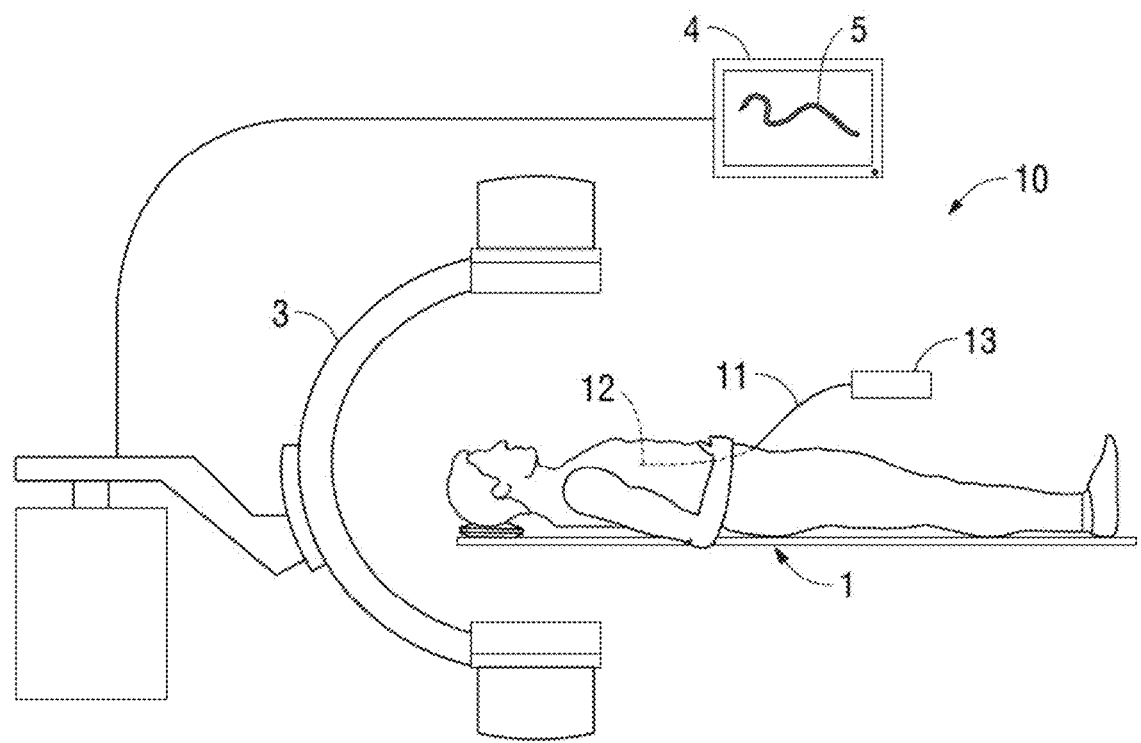
FIG. 1 is a diagram of a medical system including a medical device according to one embodiment of the disclosure.

FIG. 1 shows a system of imaging a medical device 10 within the human body 1. The medical device includes a distal end 12 configured for use within the body 1, a proximal end 11 for use outside the body 1, and a handle 13. In operation, the device 10 can be monitored with an imaging device 3 which may project the medical device's image 5 onto a monitor 4. The handle 13 may be configured to control the operation of the distal end 12.

Figure 2A:
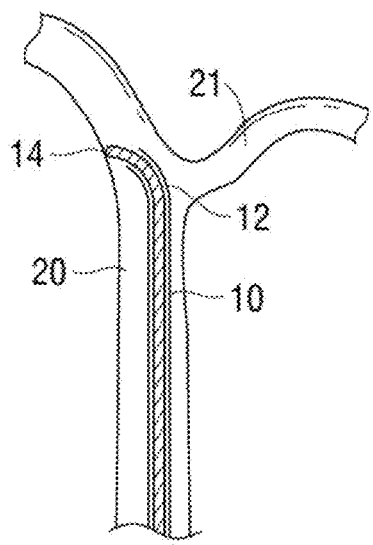
FIG. 2A is a diagram of a distal end of the medical device in an original orientation and disposed in branching segment of an endoluminal structure within the body prior to selection of a desired endoluminal structure.
Figure 2B:
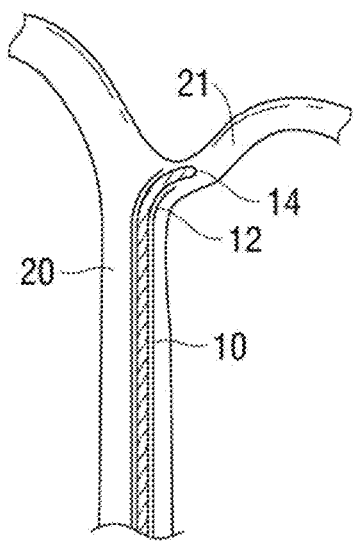
FIG. 2B is a diagram of the distal end of the medical device after selection of a branch within the branching endoluminal structure within the body.

FIG. 2A-2b show the distal end 12 of the device 10 within an endoluminal structure 20. Endoluminal structures including but not limited to blood vessels, the heart, the gastrointestinal (GI) tract, genitourinary (GU) tract, peritoneal cavity, thoracic cavity, the mediastinum, bronchial passages, subarachnoidal spaces, and the intracranial ventricular system. In FIG. 2A, a guidewire 14 is shown in the device 10 with the distal end of the device 12 directed away from a desired endoluminal branch 21. In FIG. 2B, the distal end 12 and the guidewire 14 in the endoluminal structure 20 of FIG. 2A have been rotated to point towards the desired endoluminal branch 21.

Figure 3A:
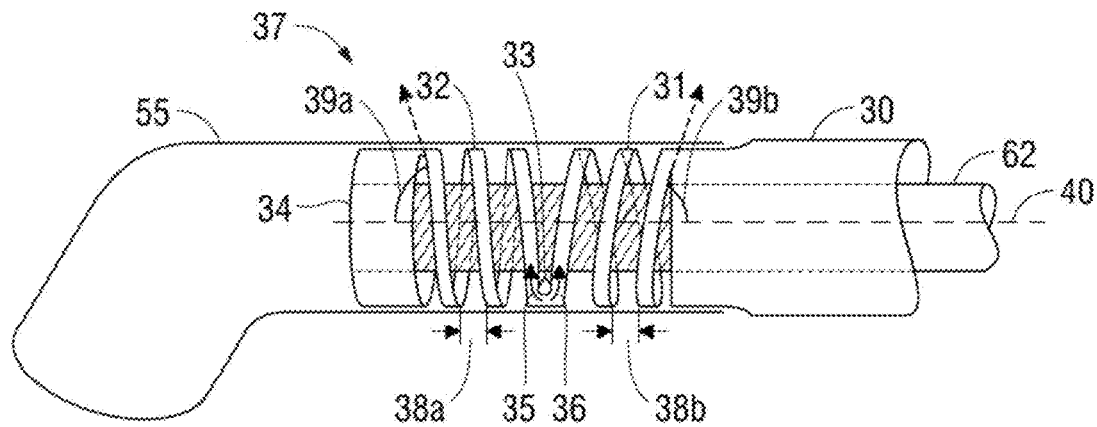
FIG. 3A is a diagram of the dual chirality helical cut into the tube with force vectors showing rotational forces during linear displacement of the distal end of the tube according to one embodiment of the present disclosure.

FIG. 3A is a diagram of a tube 30 with a dual chirality helix 37 formed by a proximal helical cut 31 and a distal helical cut 32, wherein the cuts 31, 32 are proximal and distal relative to a junction point 33. The distal cut 32 has a cut width 38a and a helical angle 39a. Similarly, the proximal cut 31 has a cut width 38b and a helical angle 39b. The cut widths 38a, 38b can range from 0.1 micrometers to 10 millimeters with the optimal range being 10-1000 microns. The helical angles 39a, 39b can range from 10 to 80 degrees. In some embodiments, the helical angles 39a, 39b range from 15 to 75 degrees. The cut widths 38a, 38b may be equal or different, and the helical angles 39a, 39b may have the same or different magnitudes. When a force 34 is applied along a long axis 40 of the tube 30, the force is converted into a force along the distal helix 35 and a force along the proximal helix 36 that are exerted on the junction point 33. The cut widths 38a, 38b and the helical angles 39a, 39b change as the dual chirality helix 37 is elongated or reduced to impart rotational motion.

Figure 3B:
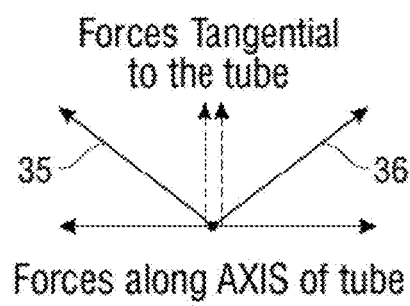
FIG. 3B is a free body diagram of the forces in FIG. 3A.

FIG. 3B shows a free body diagram of the force along the distal helix 35 and the force along the proximal helix 36 wherein the respective forces have been broken down into forces along the axis of the tube and forces tangential to the tube 30. This illustrates how the forces tangential to the tube 30 are additive and result in torquing of the junction point 33.

Figure 4A:
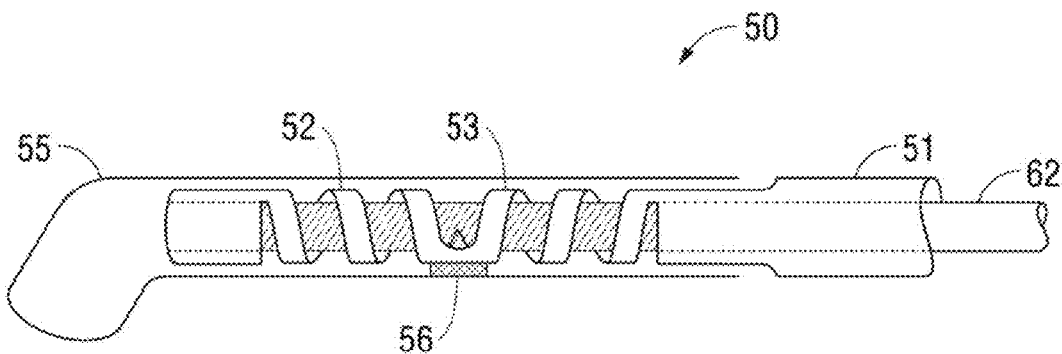
FIG. 4A is a cross sectional view along the long axis of a tube with a dual chirality helical cut without linear displacement of the distal end of the tube according to one embodiment of the present disclosure.
Figure 4B:
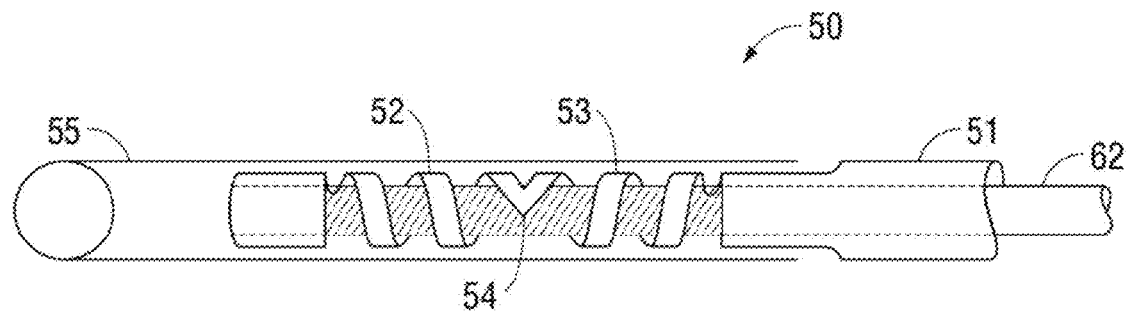
FIG. 4B is a cross sectional view along the long axis of the tube of FIG. 4A with linear displacement of the distal end of the tube.
Figure 4C:
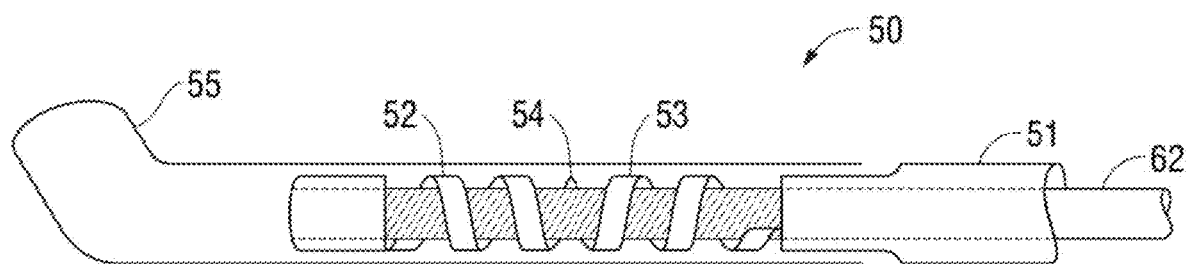
FIG. 4C is cross sectional view along the long axis of the tube of FIG. 4A with additional linear displacement of the distal end of the tube.

FIGS. 4A-4C shows the rotation of a junction point 54 between a proximal helical cut 53 and a distal helical cut 52 when the distal portion of the tube 51 is elongated. FIG. 4A shows when the distal portion of the tube 51 is not elongated. FIG. 4B shows when the distal portion of the tube 51 is elongated such that there is 90 degrees of rotation of the junction point 54 and distal segment 55 relative to their respective positions in FIG. 4A. FIG. 4C shows when the distal portion of the tube 51 is elongated such that there is 180 degrees of rotation of the junction point 54 and distal segment 55 relative to their respective positions in FIG. 4A.

Figure 5:
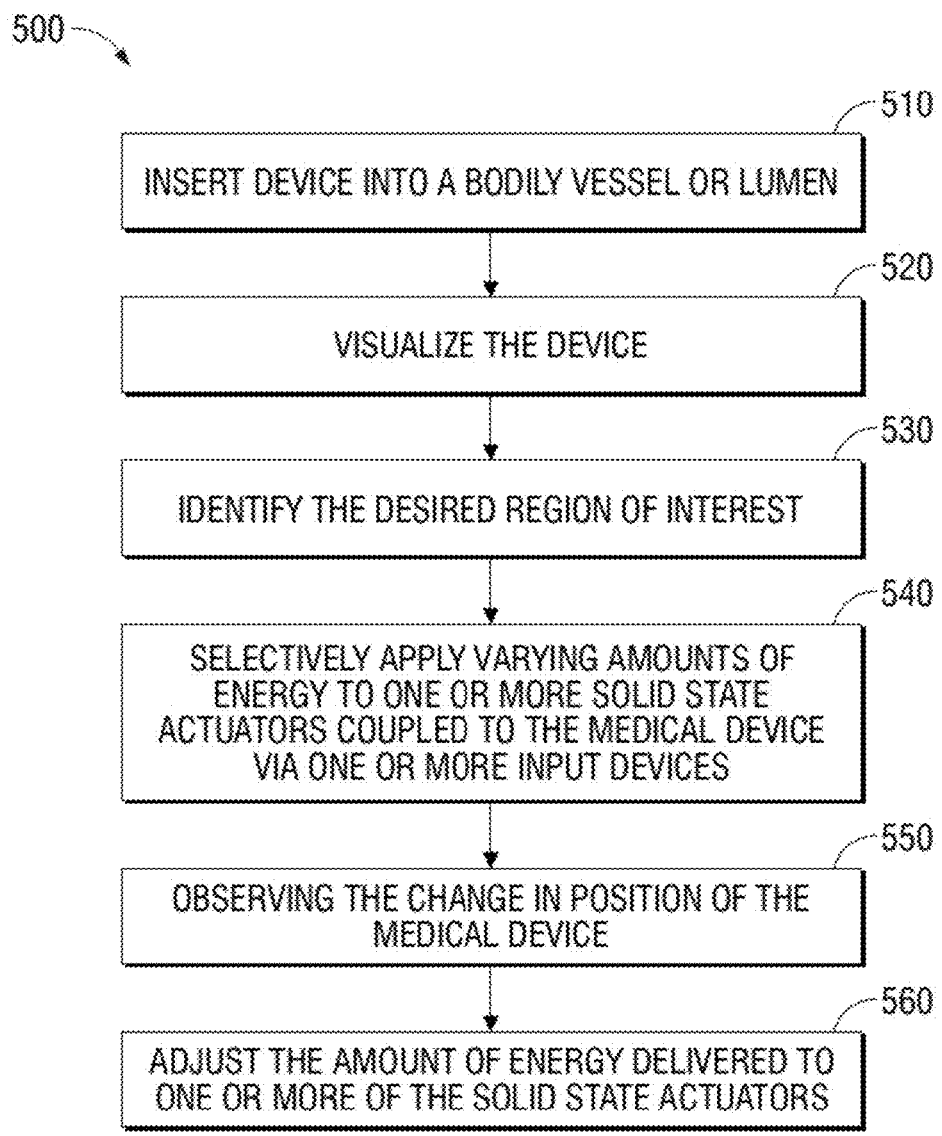
FIG. 5 is a flowchart of a method of imparting rotational motion to the distal end of the device by means of conversion of linear displacement to rotational motion via a dual chirality mechanism.
Figure 19A:
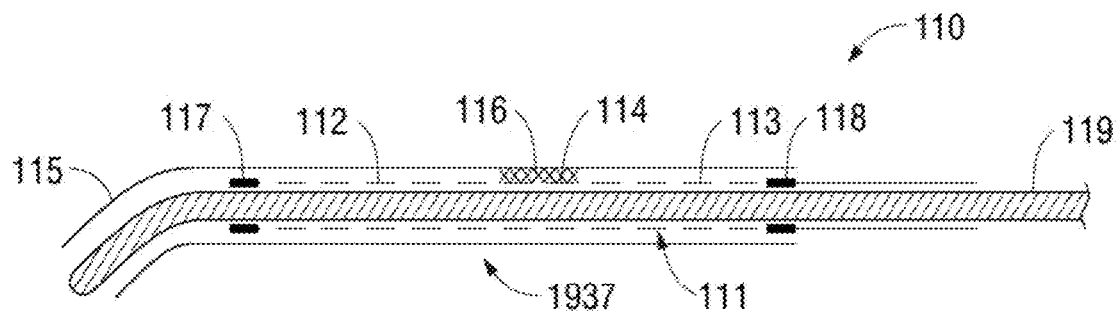
FIG. 19A is a longitudinal cross sectional view of the distal aspect of the medical device with a magnetic displacement mechanism in its resting state.

FIG. 5 shows a flow chart for a method 500 of controlling the distal end 12 of the device 10. In step 510, the device 10 is inserted into the endoluminal structure 20 of the body 1. In step 520, an image of the device 10 in the body 1 is displayed. The display may be in form of any imaging techniques for objects internal to the human body, including, but not limited to, x-ray fluoroscopy, ultrasound imaging, computed axial tomography (CAT) imaging, magnetic resonance imaging (MRI), and/or endoscopic imaging. In step 530, the region of interest is selected within the image. In step 540, longitudinal force and displacement are applied to the dual chirality helix 37 causing rotation of the distal end 12. The longitudinal force may be applied by manipulation of the sleeve 57 or wire 62. In some embodiments, the longitudinal force may be applied through the application of energy to one or more actuators coupled to the medical device, such as magnetic elements 117, 118 (FIG. 19A). In step 350, the change of position of the distal end 12 is observed on the display. In step 360, the amount of longitudinal displacement is adjusted to rotate the distal end 12 the desired degree of rotation by varying the amount of longitudinal force applied to the dual chirality helix 37 either via the sleeve 57/guidewire 62 or through energy applied to one or more actuators 117, 118.

Figure 6A:
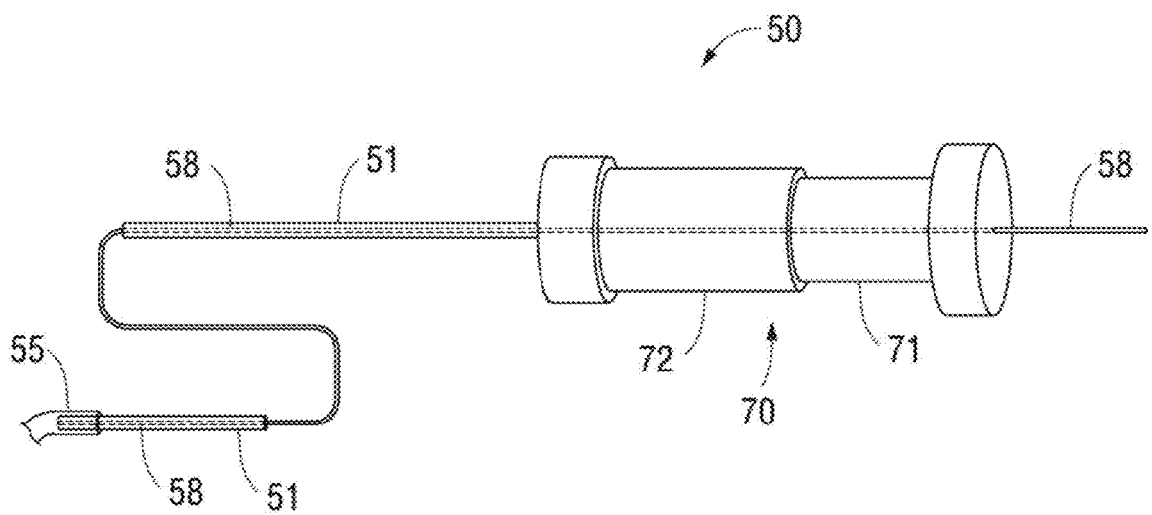
FIG. 6A is a diagram of the proximal end of the medical device according to one embodiment of the present disclosure.

FIG. 6A is a diagram of a medical device 50 according to one embodiment of the present disclosure. The device 50 includes a tube 51, a distal segment 55 coupled to the distal end of the tube 51, and a sleeve 58. The sleeve 58 is disposed within the lumen of the tube 51. The sleeve 58 can be advanced or retracted within the tube 51 to longitudinally displace the helices 52, 53. The device 50 also includes a handle 70, which is comprised of a proximal component 71 and a distal component 72 and is attached to the proximal end of the tube 51. The proximal component 71 and the distal component 72 each have cylindrical bodies, such that the proximal component 71 may be inserted into the distal component 72 and the sleeve 58 may be inserted into the proximal component 71. The proximal component 71 is reversibly coupled to the sleeve 58 and the distal component 72 is reversibly coupled to the tube 51. Each of the tube 51, the distal segment 55, and the sleeve 58 can be made of one or more of a variety of materials, including, but not limited to, polyimide, polyurethane, polyether block amides (such as Pebax®), nylon, nickel titanium (nitinol), stainless steel braiding, and hollow helical stranded tubing. In addition the distal segment 55 may have, but is not limited to, a straight, angled, and reverse curved shape.

Figure 6B:
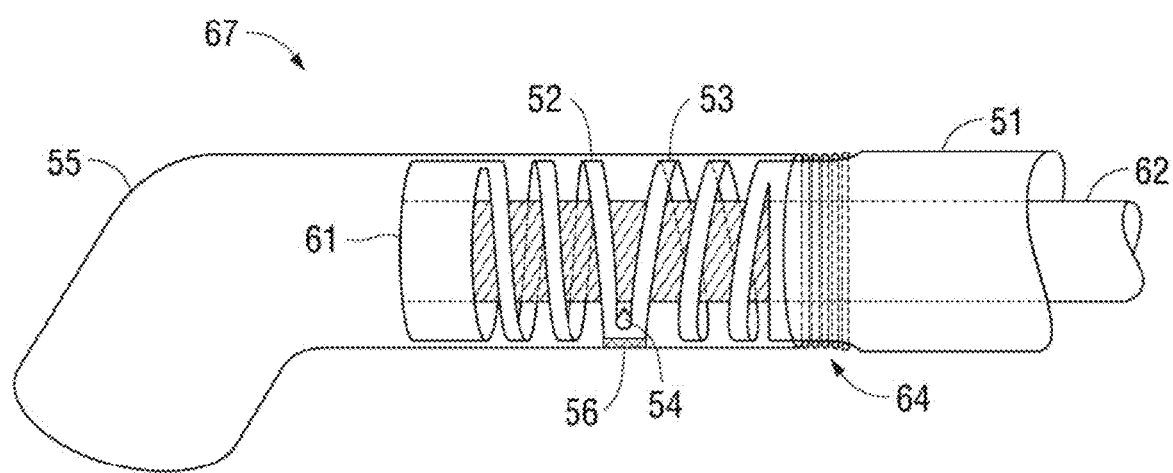
FIG. 6B is a diagram of the distal end of the medical device according to one embodiment of the present disclosure.

FIG. 6B is a close up of the distal segment and the distal end 51. As shown, a dual chirality helix 67 is formed by a distal helix 52 and a proximal helix 53 that are coupled at a junction 54. The distal and proximal helices 52, 53 are formed from the tube 51 by helical cuts, and the proximal helix 53 and the distal helix 52 converge at the junction point 54. The distal segment 55 is located circumferentially around the distal end of the tube 51 and is coupled to the junction point 54 via a coupling means 56. Suitable coupling means between the distal segment 55 and the junction 54 include, but are not limited to, one or more of: 1) adhesives (such as cyanoacrylate), 2) welding, 3) brazing, 4) soldering, and 5) mechanical linking; and additional suitable means are known by those of ordinary skill in the art. As shown, a wire 62 may be disposed within the lumen of the tube 51 and may be slideably advanced or withdrawn from the tube 51 along the long axis of the tube 51. When the wire 62 is advanced, it may abut a capped end 61 of the tube 51. Further advancement of the wire 62 after the wire abuts the capped end 61 may result in linear displacement of the dual chirality helix 67. The force associated with linear displacement of the dual chirality helix 67 produces rotational forces at the junction 54 that rotate the distal segment 55. As well known to one skilled in the art, a thin coil wire 64 can be wound around the proximal end of the distal segment 55 and coupled to the tube 51 to provide a smooth transition between the distal segment 55 and the tube 51. Advantageously, the linear motion is confined to the distal portion of the tube 51, specifically the dual chirality helix 67 and distal therefrom; thus, the entirety of the tube 51 does not require linear displacement.

Figure 7A:
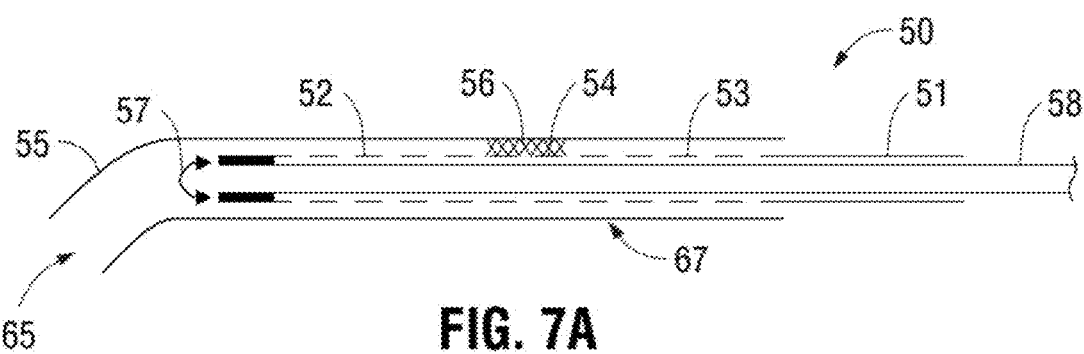
FIG. 7A is a longitudinal cross sectional view of the distal aspect of the device with an open distal end in its resting state according to one embodiment of the present disclosure.

FIG. 7A is a longitudinal cross sectional view of the device 50 with an open distal end 65 in the distal segment 55 in its resting state (i.e. no linear displacement of the dual chirality helix 67). The distal aspect of the device 50 is shown with the tube 51 wherein the dual chirality helix 67 is cut into the distal aspect of the tube 51 so as to form the proximal helix 53 and the distal helix 52. The cut section of the tube 51 may be cut entirely through the tube wall. The proximal helix 53 and the distal helix 52 are formed such that they have opposite orientations. For example, if the proximal helix 53 has a left handed orientation then the distal helix 52 has a right handed orientation or vice versa. The junction point 54 of the left and right handed helices rotates when the dual chirality helix 67 is linearly extended or compressed, resulting in the conversion of linear movement to rotational motion of the junction point 54 of the two helices. The distal segment 55 is located circumferentially around the distal aspect of the tube 51 in which the dual chirality helix 67 is cut. The distal segment 55 is coupled to the junction point 54 of the helices of the dual chirality helix 67 via a coupling means 56. The distal segment 55 can have an angulated tip so as to aid in improved navigation of the device 50. The tube 51 may include of a reduced luminal inner diameter distal to the dual chirality helix 67 that forms a shelf 57. The outer diameter of the sleeve 58 is greater than the inner diameter of the shelf 57 of the tube 51 and is less than the inner diameter of the tube 51 proximal to the shelf 57. The sleeve 58 slide-ably contacts the shelf 57 of the tube 51.

Figure 7B:
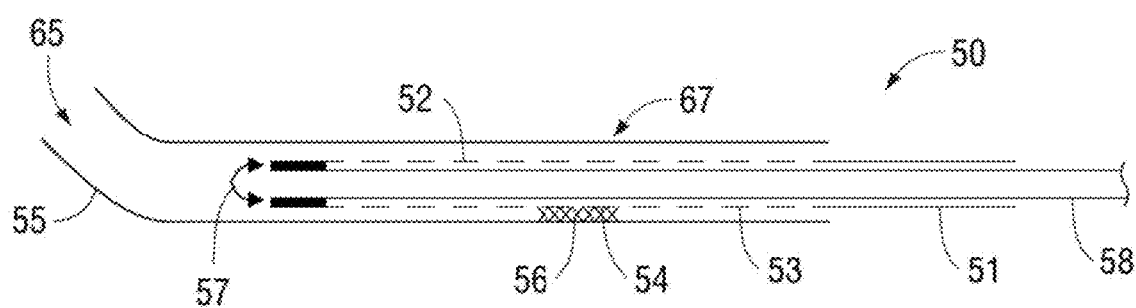
FIG. 7B is a longitudinal cross sectional view of the distal aspect of the device with an open distal end of FIG. 7A with linear displacement of the dual chirality helix via the sleeve abutting the shelf.

FIG. 7B shows the position of the distal end 65 after advancement of the sleeve 58, which linearly displaces the dual chirality helix 67. This in turn results in rotation of the junction point 54 of the proximal helix 53 and the distal helix 52 and subsequent rotation of the distal segment 55. The degree of rotation of the junction point 54 is proportional to the linear displacement of the dual chirality helix 67 of the tube 51. For illustration purposes 180 degree rotation is shown in FIG. 7B, but different degrees of rotation may be achieved by increasing or decreasing the degree of linear displacement of the sleeve 58.

Figure 8A:
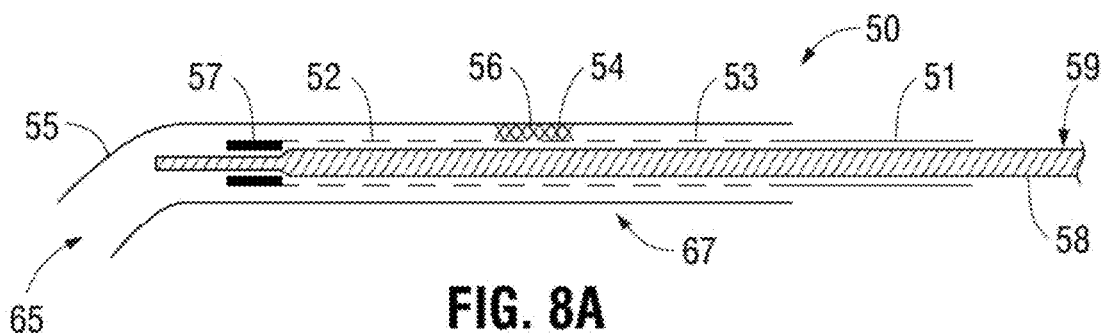
FIG. 8A is a longitudinal cross sectional view of the distal aspect of the device with an open distal end in its resting state, with an interior shelf and wire according to one embodiment of the present disclosure.

FIG. 8A shows a cross sectional view of another embodiment of the distal segment 55 of the device 50 in its resting state. The distal aspect of the device 50 is shown with the tube 51 with the distal end and the proximal end wherein the dual chirality helix 67 is cut into the distal aspect of the tube 51 so as to form the proximal helix 53 and the distal helix 52. The distal segment 55 that is coupled to the junction point 54 of the two helices of the dual chirality helix 67. The proximal helix 53 and the distal helix 52 are formed such that they have opposite orientations. For example, if the proximal helix 53 has a left handed orientation then the distal helix 52 has a right handed orientation or vice versa. By its nature, the junction point 54 of the left and right handed helices rotates when the ends of the dual chirality helix 67 are linearly extended or retracted, resulting in the conversion of linear movement to rotational motion of the junction point 54 of the two helices. The distal segment 55 is located circumferentially around the distal aspect of the tube 51 in which the dual chirality helix 67 is cut. The distal segment 55 is coupled to the junction point 54 of the helices of the dual chirality helix 67 via a coupling means 56. The distal segment 55 can have an angulated tip so as to aid in improved navigation of the device 50. The tube 51 includes the shelf 57 with its reduced luminal inner diameter distal to the dual chirality helix 67. The outer diameter of the sleeve 58 is greater than the inner diameter of the shelf 57 of the tube 51 and is less than the inner diameter of the tube 51 proximal to said shelf 57. The device 50 also includes a wire 59. The wire 59 is disposed in the lumen of the tube 51 and a distal portion of the wire has a reduced diameter so that the distal portion of the wire 59 is dimensioned to pass through the reduced distal diameter of the shelf 57. The remainder of the wire 59, or at least the portion adjacent to the distal portion has a diameter that is greater than the inner diameter of the shelf 57. Thus, the wire 59 with reduced distal diameter slide-ably abuts and engages said shelf 57 of the tube 51.

Figure 8B:
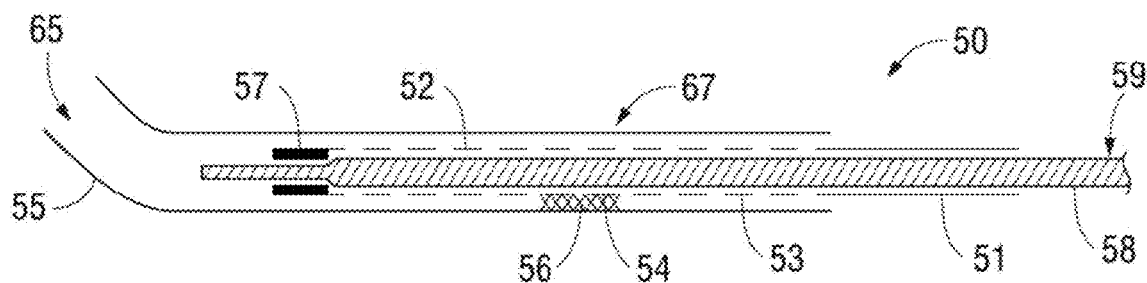
FIG. 8B is a longitudinal cross sectional view of the distal aspect of the device with an open distal end of FIG. 8A with linear displacement of the dual chirality helix via the nonreduced diameter of the wire abutting the shelf.

In FIG. 8B, the wire 59 is shown advanced in the tube 51 and linearly displacing the dual chirality helix 67 as depicted in FIG. 8B. The linear displacing causes rotation of the junction point 54 of the proximal helix 53 and the distal helix 52 and subsequent rotation of the distal segment 55. The degree of rotation of the distal segment 55 is proportional to the linear displacement of the dual chirality helix 67 of the tube 51. For illustration purposes 180 degree rotation is shown in FIG. 8B, but different degrees of rotation may be achieved by increasing or decreasing the degree of linear displacement of the wire 59.

Figure 9A:
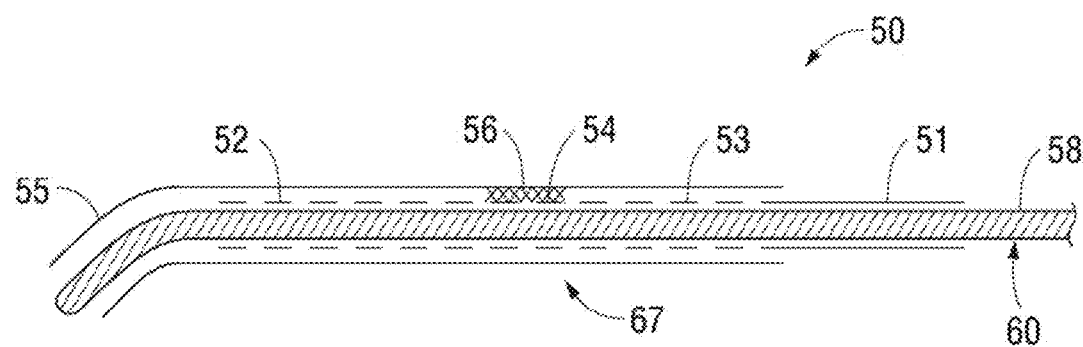
FIG. 9A is a longitudinal cross sectional view of the distal aspect of the device with an open distal end in its resting state with a wire with an expandable member.

FIG. 9A shows a cross sectional view of another embodiment of the distal segment 55 of the device 50 in its resting state with an open distal end 65. The distal aspect of the device 50 is shown with the tube 51 with its distal end and its proximal end wherein a dual chirality helix 67 is cut into the distal aspect of the tube 51 so as to form the proximal helix 53 and the distal helix 52. The distal segment 55 is coupled to the junction point 54 of the two helices of the dual chirality helix 67. The proximal helix 53 and the distal helix 52 are formed such that they have opposite orientations. For example, if the proximal helix 53 has a left handed orientation then the distal helix 52 has a right handed orientation or vice versa. By its nature, the junction point 54 of the left and right handed helices rotates when the ends of the dual chirality helix 67 are linearly extended or retracted, resulting in the conversion of linear movement to rotational motion of the junction point 54 of the two helices. The distal segment 55 is located circumferentially around the distal aspect of the tube 51 in which the dual chirality helix 67 is cut. The distal segment 55 is coupled to the junction point 54 of the helices of the dual chirality helix 67 via a coupling means 56. The distal segment 55 can have an angulated tip so as to aid in improved navigation of the device 50. A wire 60 is disposed coaxially within the lumen of the tube 51, and the wire 60 is reversibly expandable.

Figure 9B:
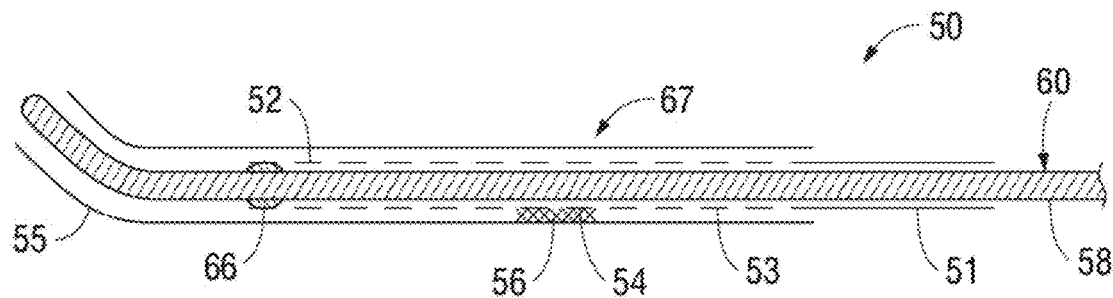
FIG. 9B is a longitudinal cross sectional view of the distal aspect of the device with an open distal end of FIG. 9A with linear displacement of the dual chirality helix via the expanded member of the wire abutting the distal end of the dual chirality helix.

FIG. 9B shows the device 50 of FIG. 9A with the wire 60 expanded so that the expandable member 66 is extended to or greater than the diameter of the tube 51. When the reversibly expandable member 66 is expanded, it engages the distal end of the tube 51. When the wire 60 is advanced while the reversibly expanded member 66 is in its expanded state, the wire 60 induces linear displacement in the dual chirality helix 67. This in turn results in rotation of the junction point 54 of the proximal helix 53 and the distal helix 52 and subsequent rotation of the distal segment 55. The degree of rotation is proportional to the linear displacement of the dual chirality helix 67 of the tube 51. For illustration purposes 180 degree rotation is shown in FIG. 9B, but different degrees of rotation may be achieved by increasing or decreasing the degree of linear displacement of the sleeve 58. When the reversibly expandable member 66 is collapsed, the outer diameter of the wire 60 is less than the inner diameter of the lumen of the tube 51 and thus the wire is able to move freely within the lumen of the tube 51, as shown in FIG. 9A.

Figure 10A:
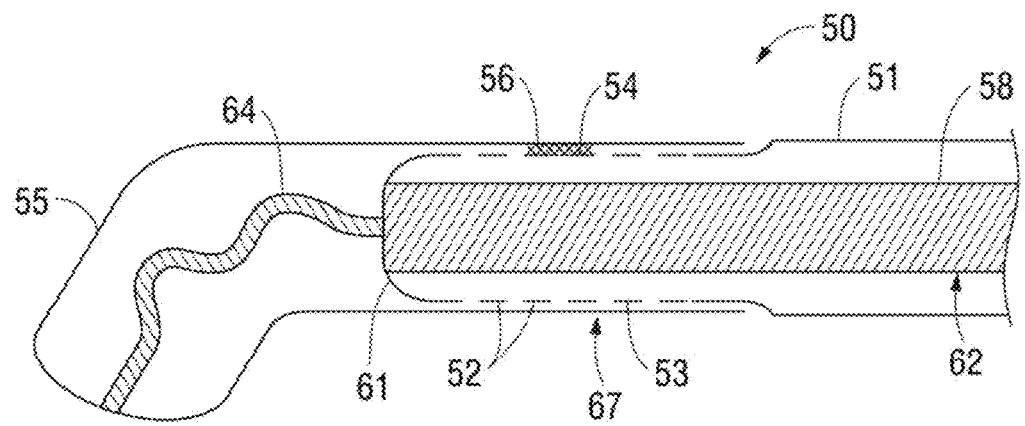
FIG. 10A is a longitudinal cross sectional view of the distal aspect of the medical device with a capped distal end in its resting state.
Figure 10B:
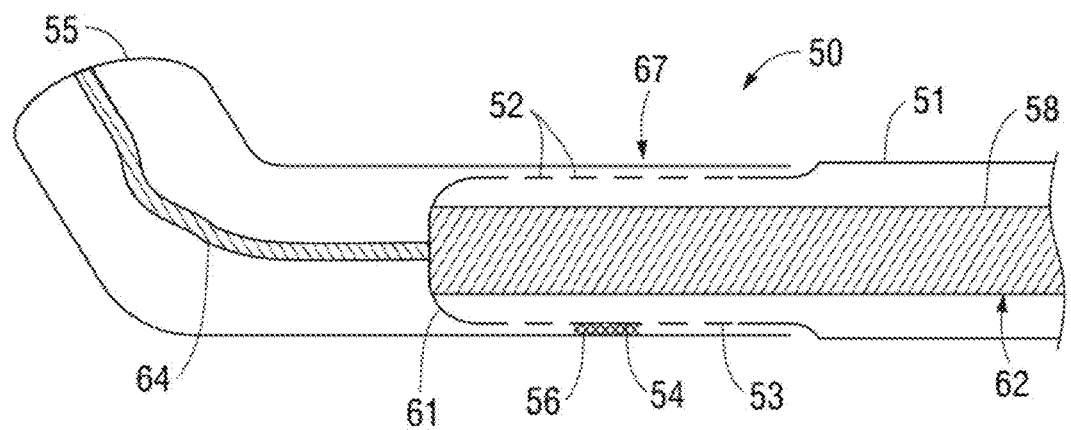
FIG. 10B is a longitudinal cross sectional view of the distal aspect of the medical device with a capped distal end of FIG. 10A with linear displacement of the dual chirality helix via the wire abutting the capped end.

FIG. 10A shows a cross sectional view of another embodiment of the distal aspect of the device 50 in its resting state that includes a capped end 61 on the tube 51. The distal aspect of the device 50 is shown with the tube 51 having the distal end and the proximal end wherein the dual chirality helix 67 is cut into the distal aspect of the tube 51 so as to form the proximal helix 53 and the distal helix 52. The distal segment 55 is coupled to the junction point 54 of the two helices of the dual chirality helix 67. The proximal helix 53 and the distal helix 52 are formed such that they have opposite orientations. For example, if the proximal helix 53 has a left handed orientation then the distal helix 52 has a right handed orientation or vice versa. By its nature, the junction point 54 of the left and right handed helices rotates when the ends of the dual chirality helix 67 are linearly extended or retracted, resulting in the conversion of linear movement to rotational motion of the junction point 54 of the two helices. The distal segment 55 is located circumferentially around the distal aspect of the tube 51 in which the dual chirality helix 67 is cut. The distal segment 55 is coupled to the junction point 54 of the helices of the dual chirality helix 67 via a coupling means 56. The distal segment 55 can have an angulated tip so as to aid in improved navigation of the device 50. A wire 62 is disposed coaxially within the lumen of the tube 51. The wire 62 contacts the capped end 61, and advancing the wire 62 applies force against the capped end 61 and linearly displaces the dual chirality helix 67 as shown in FIG. 10B. This in turn results in rotation of the junction point 54 of the proximal helix 53 and the distal helix 52 and subsequent rotation of the distal segment 55. The degree of rotation is proportional to the linear displacement of the dual chirality helix 67 of the tube 51. For illustration purposes 180 degree rotation is shown in FIG. 10B, but different degrees of rotation may be achieved by increasing or decreasing the degree of linear displacement of the wire 62.

Figure 11A:
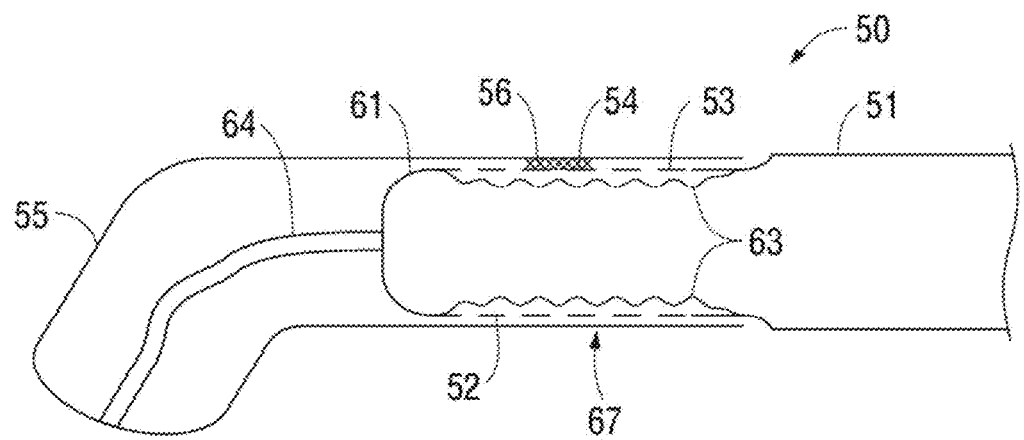
FIG. 11A is a longitudinal cross sectional view of the distal aspect of the device with a capped distal end in its resting state configured to receive an injection of fluid into the lumen of the tube.
Figure 11B:
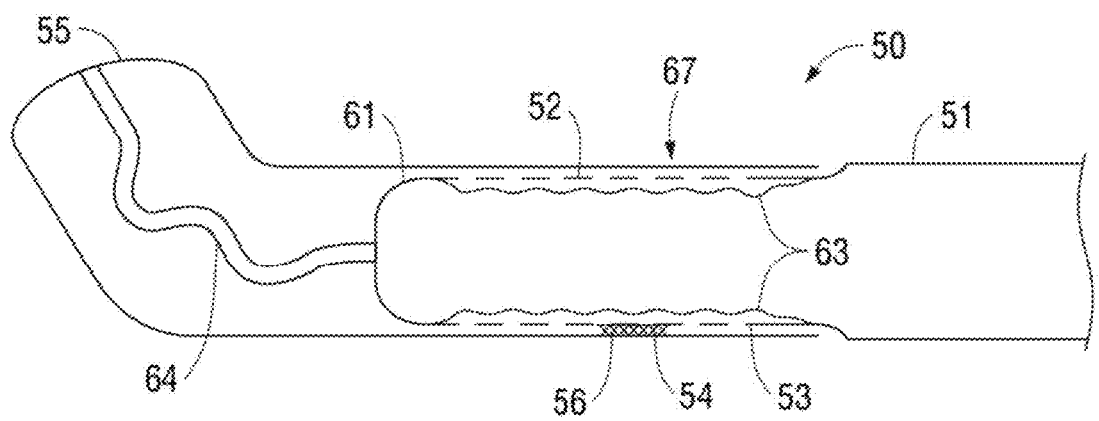
FIG. 11B is an enlarged longitudinal cross sectional view of the distal aspect of the device with a capped distal end of FIG. 11A with linear displacement of the dual chirality helix via the injection of fluid into the lumen of the tube.

FIG. 11A shows a cross sectional view of another embodiment of the distal aspect of the device 50 in its resting state with the capped end 61 of the tube 51. The distal aspect of the device 50 is shown with the tube 51 having the distal end and the proximal end wherein the dual chirality helix 67 is cut into the distal aspect of the tube 51 so as to form the proximal helix 53 and the distal helix 52, and the distal segment 55 is coupled to the junction point 54 of the two helices of the dual chirality helix 67. The proximal helix 53 and the distal helix 52 are formed such that they have opposite orientations. For example, if the proximal helix 53 has a left handed orientation then the distal helix 52 has a right handed orientation or vice versa. By its nature, the junction point 54 of the left and right handed helices rotates when the ends of the dual chirality helix 67 are linearly extended or retracted, resulting in the conversion of linear movement to rotational motion of the junction point 54 of the two helices. The distal segment 55 is located circumferentially around the distal aspect of the tube 51 in which the dual chirality helix 67 is cut. The distal segment 55 is coupled to the junction point 54 of the helices of the dual chirality helix 67 via a coupling means 56. The tip of the distal segment 55 can have an angulated tip so as to aid in improved navigation of the device 50. A membrane or liner 63 is disposed within the lumen of the tube 51. Injection of fluid within the lumen of the tube 51 expands the membrane 63, and imparts linear displacement on the dual chirality helix 67 as shown in FIG. 11B. This in turn results in rotation of the junction point 54 of the proximal helix 53 and the distal helix 52 and subsequent rotation of the distal segment 55. The degree of rotation is proportional to the linear displacement of the dual chirality helix 67 of the tube 51. The injection or withdrawal of fluid from the interior of the membrane 63 can be precisely controlled, which allows for fine adjustments to the rotation of the distal segment 55. The fine adjustments enable the medical device 100 to be used with vasculature that has small vessels and allowed for selections of specific branches with little risk of impacting the vascular walls due to whip or overshooting a selected branch during rotation of the distal segment 55. Additionally, the fine adjustments enable precision positioning of auxiliary equipment, such as a lamp for illumination of the interior of the body, where discrete and/or subtle adjustments in rotation angle are beneficial or necessary. It is noted that fine adjustments also reduce the buildup of potential energy in the distal segment 55 that could result in whip if release too suddenly. For illustration purposes 180 degree rotation is shown in FIG. 11B, but different degrees of rotation may be achieved by increasing or decreasing the degree of linear displacement dual chirality helix 67 with the inflation/deflation of the membrane 63. In some embodiments, the a single helix 203 may be substituted for the dual chirality helix 67. (See FIGS. 23-25).

Figure 12A:
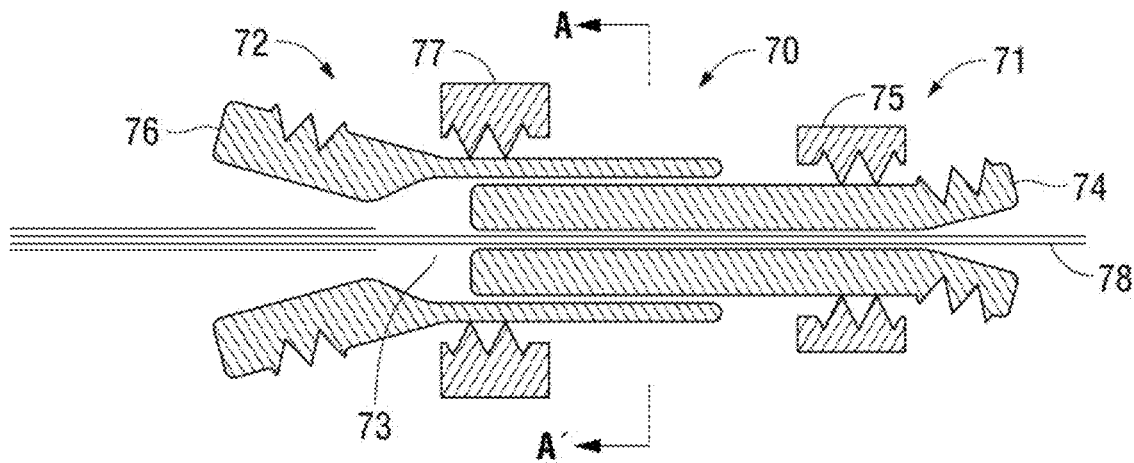
FIG. 12A is a longitudinal cross sectional view of the handle with controlled linear displacement in an open state.

FIG. 12A shows a cross sectional view of a handle 70 that is suitable as an embodiment of the handle 13 shown in FIG. 1 for grasping the proximal end 11 of the device 10. The handle 70 may include a proximal component 71 and a distal component 72, wherein the proximal component and 71 and a distal component 72 are coaxial with one another. The proximal component 71 and the distal component 72 may be made of one or more of a variety of materials, including, but not limited to, one or more of: polycarbonate and metal. The distal component 72 has a cylinder 73 which is configured to slidably receive the proximal aspect of the tube 51 and the sleeve 58 or a wire 78. The proximal component 71 and the distal component 72 configured to move relative to one another along the long axis of the handle 70.

Figure 12B:
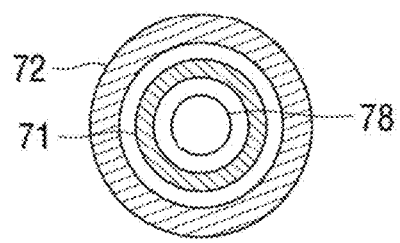
FIG. 12B is a transverse cross sectional view of the handle with controlled linear displacement through A-A' in FIG. 12A.

A distal fitting 76 is located on the distal end of the distal component 72. This distal fitting 76 is flared away from the lumen 73. A proximal fitting 74 is located on the distal end of the proximal end of the proximal component 71 and is also flared away from the cylinder 73. A distal compression nut 77 is fitted about the outer diameter of the distal component 72. The distal fitting 76 is threaded such that the threads mate with the distal compression nut 77. A proximal compression nut 75 is fitted about the outer diameter of the proximal component 71. The proximal fitting 74 is threaded such that the threads mate with the proximal compression nut 75. FIG. 12B shows a short axis cross section through line A-A'. The proximal component 71 and the distal component 72 are coaxial with each other and the wire 78.

Figure 13:
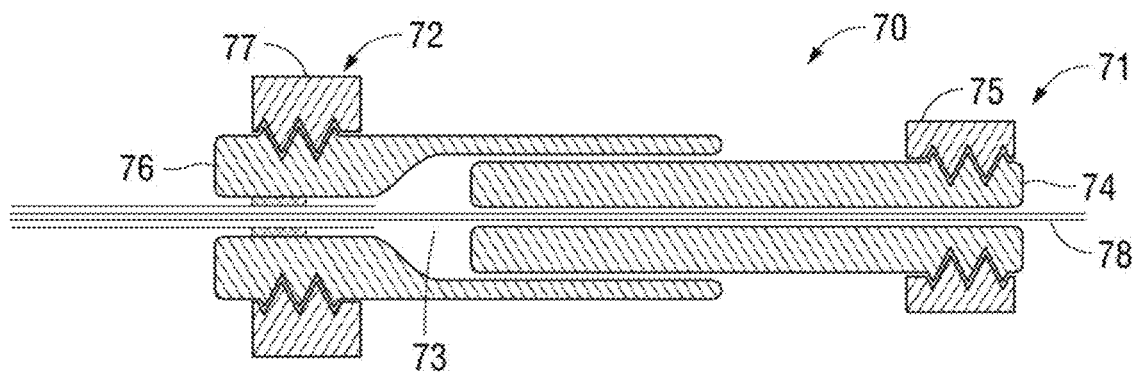
FIG. 13 is a longitudinal cross sectional view of the handle with controlled linear displacement in a closed state.

FIG. 13 shows a cross section through the longitudinal axis of the handle 70 with the proximal compression nut 75 and distal compression nut 77 engaged with the threaded portion of the proximal fitting 74 and the threaded portion of the distal fitting 76, respectively, such that the distal fitting 76 and the proximal fitting 74 are compressed towards the cylinder 73, rather than flared as in FIG. 12A.

Figure 14A:
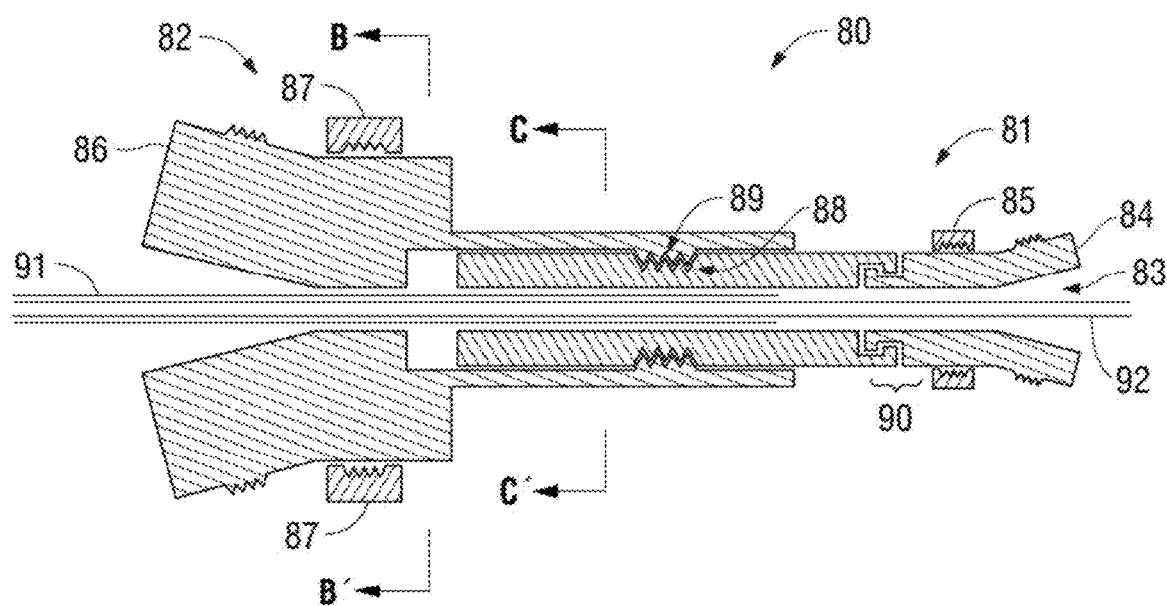
FIG. 14A is a longitudinal cross sectional view of the handle with controlled linear displacement in an open state.

FIGS. 14A-14C and FIGS. 15A-15C show a handle 80 that is suitable as another embodiment of the handle 13 shown in FIG. 1 for grasping the proximal end 11 of the device 10. FIG. 14A shows the handle 80 including a proximal component 81 and a distal component 82 wherein the proximal component 81 and a distal component 82 are coaxial with one another. The proximal component 81 and the distal component 82 may be made of one or more of a variety of materials, including, but not limited to, one or more of: polycarbonate and metal. The distal aspect of the proximal component 81 has a threaded portion herein referred to as proximal component threads 88 and the proximal portion of the distal component 82 has a threaded portion herein referred to as distal component threads 89. The proximal component 81 and the distal component 82 are capable of displacement with respect to one another along the long axis of the handle 80 via rotation of the proximal component 81 with respect to the distal component 82. A swivel 90 is disposed within the proximal component 81 such that the proximal fitting 84 and the proximal component 81 may rotated relative to one another. The handle 80 has a lumen 83 that is dimensioned to receive the proximal aspect of a tube 91 and a sleeve or wire 92 that is disposed coaxially within the tube 91 for at least part of its length.

A distal fitting 86 is located on the distal end of the distal component 82. The distal end of the distal fitting 86 is flared away from the lumen 83. A proximal fitting 84 is located on the proximal end of the proximal component 81. The proximal end of the proximal fitting is flared away from the lumen 83. A distal compression nut 87 is fitted about an outer diameter of the distal component 82. The distal fitting 86 is threaded such that the threads mate with the distal compression nut 87. A proximal compression nut 85 is fitted about the outer diameter of the proximal component 81. The proximal fitting 84 is threaded such that the threads mate with the proximal compression nut 85.

Figure 14B:
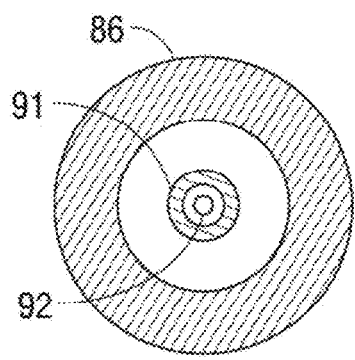
FIG. 14B is a transverse cross sectional view of the handle with controlled linear displacement through B-B' in FIG. 14A.
Figure 14C:
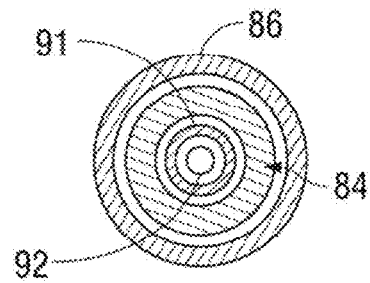
FIG. 14C is a transverse cross sectional view of the handle with controlled linear displacement through C-C' in FIG. 14A.

FIG. 14B shows a short axis cross section through line B-B' of FIG. 14A, which passes through the distal fitting 86. The longitudinal displacer, such as sleeve or wire 92, is shown coaxial with the tube 91, and both the sleeve or wire 92 and the tube 91 are coaxial with the distal fitting 86. Likewise, FIG. 14C shows a short axis cross section through line C-C' of FIG. 14A, which passes through the proximal fitting 84 where it overlaps the distal fitting 86. The sleeve or wire 92 is shown coaxial with the tube 91, as well as, the proximal fitting 84 and the distal fitting 86.

FIG. 15A shows a cross section through the longitudinal axis of the handle 80 with the proximal compression nut 85 and the distal compression nut 87 engaged with the threaded portion of the proximal fitting 84 and the threaded portion of the distal fitting 86, respectively, such that the distal fitting 86 and the proximal fitting 84 are compressed towards the lumen 83. FIG. 15B shows a short axis cross section through line B-B' of FIG. 15A, which passes through the distal fitting 86. The sleeve or wire 92 are shown coaxial with the tube 91, and both the sleeve or wire 92 and the tube 91 are coaxial with the distal fitting 86. Likewise, FIG. 15C shows a short axis cross section through line C-C' of FIG. 15A, which passes through the proximal fitting 84 where it overlaps the distal fitting 86. The sleeve or wire 92 is shown coaxial with the tube 91, as well as, the proximal fitting 84 and the distal fitting 86.

Figure 16:
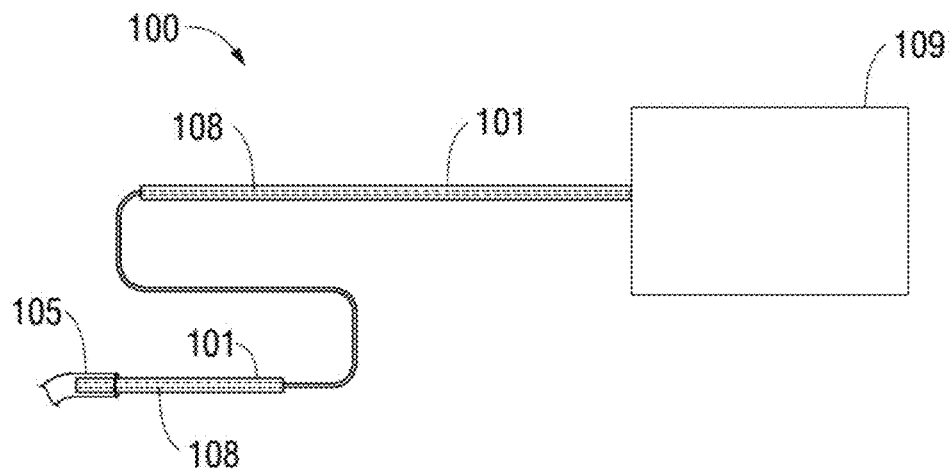
FIG. 16 is a diagram of a second embodiment of the medical device wherein the dual chirality helix is displaced via the tube undergoing a shape transformation in response to a change in the surrounding environment.

FIG. 16 is a diagram of another embodiment of the apparatus that includes a medical device 100 wherein a dual chirality helix 1709 (see FIG. 17A) is cut into the distal aspect of the tube 101. The tube 101 includes a material, including but not limited to nickel titanium (nitinol), selected to undergo a shape transformation in response to a change in the local environment, such that there is elongation of the dual chirality helix 1709. A conduit 108 is disposed within the tube 101. The conduit 108 may be connected to a source 109 for an agent for changing the local environment is located within the tube 101. Exemplary agents for changing the local environment may include, but are not limited to, one or more of: a battery for Joule heating or altering the magnetic field, a radiofrequency generator, a microwave generator, a heat source, a light source, and a chemical source of releaseable ions. In one embodiment, the dual chirality helix 1709 may linearly elongate when exposed to an increase in temperatures. The elongation may take place over a temperature range of 40 degrees C. to 90 degrees C. In some embodiments, the temperature range for elongation may be between 40 degrees C. and 60 degrees C. A distal segment 105 is coupled to the distal aspect of the tube 101.

Figure 17A:
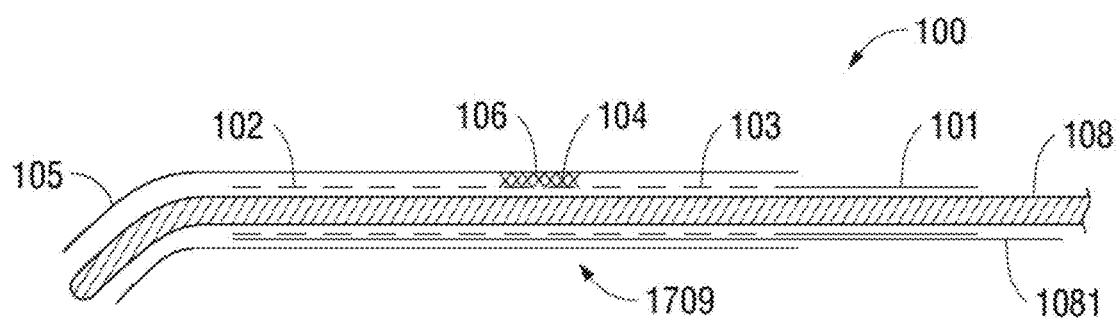
FIG. 17A is a longitudinal cross sectional view of the distal aspect of the device in its resting state according to another embodiment of the present disclosure.

FIG. 17A is a longitudinal cross sectional view of the distal aspect of one embodiment of the medical device 100 in its resting state where there is no linear displacement of the dual chirality helix 1709. The distal aspect of the medical device 100 is shown with the tube 101 with a distal end and a proximal end wherein the dual chirality helix 1709 is cut into the distal aspect of the tube 101 so as to form a proximal helix 103 and a distal helix 102. The conduit 108 is located coaxially within the lumen of the tube 101, and a distal segment 105 is coupled to the junction point 104 of the two helices 102, 103 of the dual chirality helix 1709. The proximal helix 103 and the distal helix 102 are formed such that they have opposite orientations. For example, if the proximal helix 103 has a left handed orientation then the distal helix 102 has a right handed orientation or vice versa.

By its nature, the junction point 104 of the left and right handed helices rotates when the ends of the dual chirality helix 1709 are linearly extended or retracted, resulting in the conversion of linear movement to rotational motion of the junction point 104 of the two helices 102, 103. The distal segment 105 is located circumferentially around the distal aspect of the tube 101 in which the dual chirality helix 1709 is cut. The distal segment 105 is coupled to the junction point 104 of the helices 102, 103 of the dual chirality helix 1709 via a coupling means 106 including, but not limited to, one or more of: 1) adhesives (such as cyanoacrylate), 2) welding, 3) brazing, 4) soldering, and 5) mechanical linkage. The distal segment 105 can have an angulated tip so as to aid in improved navigation of the medical device 100. Some embodiments may include an optional means for counteracting shape transformation of the tube 101, including, but not limited to, coupling the conduit 108 to the distal end of the tube 101. In one embodiment, the tube 101 has a distal diameter that is slightly greater than the rest of the tube 101 and a thin wire 1081 is run in the tube 101 adjacent to said conduit 108, such as in the annular space between the tube 101 and the conduit 108. When tension is applied to the conduit 108 with the thin wire 1081 in place, tension on the thin wire 1081 counteracts the linear displacement of the dual chirality helix 1709.

Figure 17B:
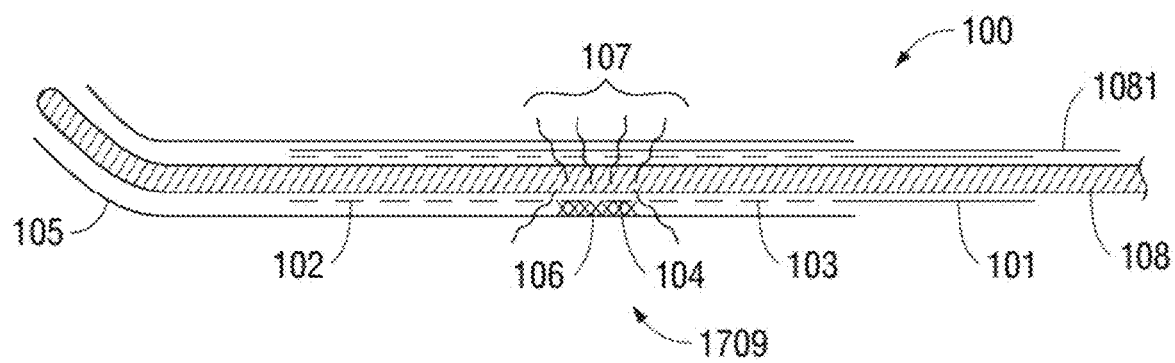
FIG. 17B is a longitudinal cross sectional view of the distal aspect of the medical device of FIG. 17A with linear displacement of the dual chirality helix secondary to shape transformation of the tube.

FIG. 17B shows a longitudinal cross sectional view of the distal aspect of the embodiment of FIG. 17A when a change in the local environment 107 is delivered to the environment around the dual chirality helix 1709, wherein local in proximity to the dual chirality helix 1709. An exemplary change in the local environment may be a change in local temperature that can cause part of the medical device 100 to undergo shape transformation due to heat expansion or contraction. The change in the local environment may include one or more of changes in temperature, pH, magnetic field strength, ion concentration, and light. The change in the local environment 107 may result in a shape transformation of the proximal helix 103 and distal helix 102 and cause linear displacement of the dual chirality helix 1709. The junction point 104 of the proximal helix 103 and the distal helix 102 rotates and, in turn, rotates the distal segment 105. The degree of rotation of the distal segment 105 is proportional to the linear displacement of the dual chirality helix 1709 of the tube 101. For illustration purposes 180 degree rotation is shown. In some embodiments, the distal helix 102 and the proximal helix 103 may be comprised of a shape member alloy (such as, but not limited to, nitinol) or a shape memory polymer (such as, but not limited to, block copolymer of polyethylene terephthalate (PET) and polyethyleneoxide (PEO)).

In some embodiments, the thin wire 1081 may be used to restrain the longitudinal movement of the junction point 104. Thus, the user, by releasing tension on the wire 1081 may allow the junction point 104 to extend longitudinally in a controlled fashion.

Figure 18:
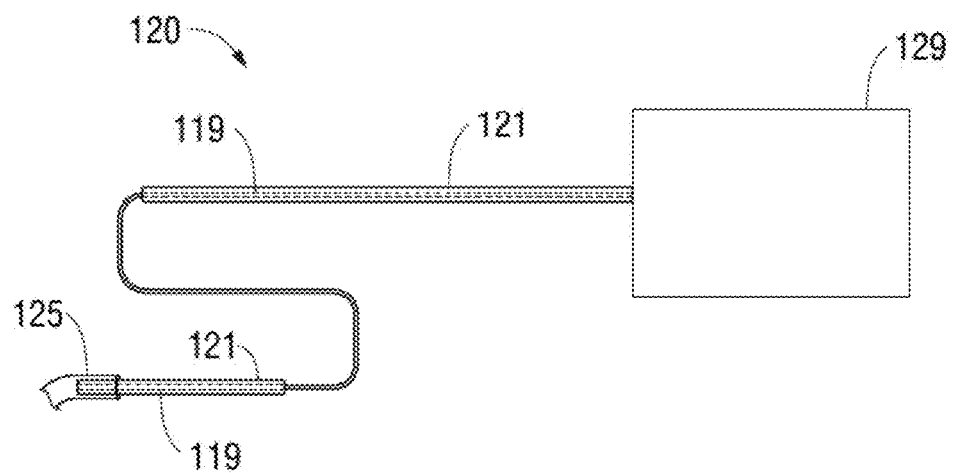
FIG. 18 is a diagram of another embodiment of the medical device wherein the dual chirality helix is displaced via magnetic forces.

FIG. 18 is a diagram of another embodiment of the apparatus that includes a medical device 120 wherein a dual chirality helix 1937 (see FIG. 19A) is cut into a distal aspect of a tube 121 and wherein another means for linear displacement of the tube containing a dual chirality helical cut is provided. The tube 212 can be made of one or more of a variety of materials, including, but not limited to, polyimide, polyurethane, polyether block amides (such as Pebax®), nylon, nickel titanium (nitinol), stainless steel braiding, coiled wire and hollow helical stranded tubing. The proximal end of the medical device 120 is connected to a source of electricity 129, such as a battery, wherein energy is able to be transmitted along the device via conductive elements, such as thin wires. A distal segment 125 is coupled to the distal aspect of the tube 121. The linear displacement means includes, but is not limited to, repulsion or attraction of electrical fields or magnetic fields between elements within or coupled to the distal end of the dual chirality helix 1937 that is capable of emitting a permanent or inducible magnetic field, and elements proximate to, but not in direct contact with the distal end of the dual chirality helix 1937 that is capable of emitting a permanent or inducible magnetic field. Examples of these elements include, but are not limited to, rare earth magnets, coiled wire capable of passage of electrical current, electret, and plate capacitor. Examples of methods for applying opposing electrical or magnetic fields along or proximate to the region of the dual chirality helix 1937 include but are not limited to 1) applying a permanent electrical or magnetic charge on one end of the dual chirality helix 1937 and a variable, inducible charge on the opposite end of the dual chirality helix 1937; 2) applying an inducible electrical or magnetic charge on one end of the dual chirality helix 1937 and a variable, inducible electrical or magnetic charge on the opposite end of the dual chirality helix 1937; 3) applying an electrical or magnetic charge on one end of the dual chirality helix 1937 and an electrical or magnetic charge on a portion of a guidewire 119 proximate to the dual chirality helix 1937.

FIG. 19A shows a longitudinal cross sectional view of the distal aspect of a medical device 110 suitable for use as an alternative for the distal aspect of the medical device 120 of FIG. 18 in its resting state. The distal aspect of the medical device 110 is shown with a tube 111 with a distal end and a proximal end wherein a dual chirality helix 1937 is cut into the distal aspect of the tube 111 so as to form a proximal helix 113 and a distal helix 112, a distal magnetic element 117, a proximal magnetic element 118, and a distal segment 115 that is coupled to the junction point 114 of the two helices 112, 113 of the dual chirality helix 1937. Each of the magnetic elements 117, 118 may be biocompatible. Exemplary magnetic elements 117, 118 may include rare earth magnets and coil-electromagnets. The types of electromagnets used for magnetic elements 117 and 118 may be the same or different. The magnetic elements 117, 118 are selected such that the force of attraction/repulsion between the magnetic elements 117, 118, when energized, is sufficient to overcome the spring force of the dual chirality helix 1937. The magnetic elements 117, 118 may be connected to the tube 111 in proximity to opposite ends of the dual chirality helix 1937, so that magnetic force between the magnetic elements 117, 118, when energized, will elongate or compress the dual chirality helix 1937 longitudinally, depending on the configuration of the magnetic elements 117, 118 (attractive or repulsive magnetic force). In this manner, the energizing of one or both of the magnetic elements 117, 118, by elongating or compressing the dual chirality helix 1937, imparts rotational force on the distal segment 115 without rotating the guidewire 119. Exemplary magnetic elements 117, 118 may include permanent magnets (such as rare earth magnets) and electromagnets. In some embodiments, one of the magnetic elements 117, 118 may be a ferromagnetic material that response to a magnetic field is not itself magnetic. The proximal helix 113 and the distal helix 112 are formed such that they have opposite orientations. For example, if the proximal helix 113 has a left handed orientation then the distal helix 112 has a right handed orientation or vice versa. By its nature, the junction point 114 of the left and right handed helices rotates when the ends of the dual chirality helix 1937 are linearly extended or retracted, resulting in the conversion of linear movement to rotational motion of the junction point 114 of the two helices. The distal segment 115 is located circumferentially around the distal aspect of the tube 111 in which the dual chirality helix 1937 is cut. The distal segment 115 is coupled to the junction point 114 of the helices 112, 113 of the dual chirality helix 1937 via a coupling means 116. The coupling means 116 may include, but is not limited to, one or more of: 1) adhesives (such as cyanoacrylate), 2) welding, 3) brazing, 4) soldering, and 5) mechanical linking. The distal segment 115 can have an angulated tip so as to aid in improved navigation of the medical device 110.

Figure 19B:
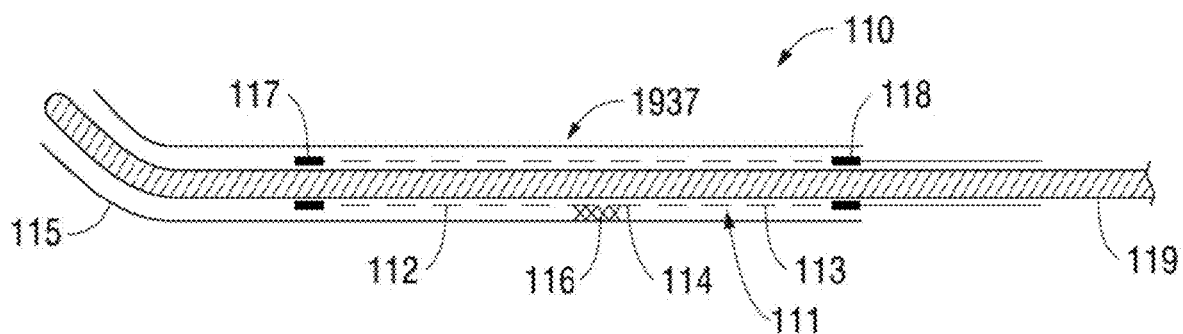
FIG. 19B is a longitudinal cross sectional view of the distal aspect of the medical device with the magnetic displacement mechanism of FIG. 19A with linear displacement of the dual chirality helix secondary magnetic forces imparted on the tube.

FIG. 19B shows a longitudinal cross sectional view of the distal aspect of the medical device 110 from FIG. 19A when the magnetic field at least one of the distal magnetic element 117 and the proximal magnetic element 118 is changed, which causes linear displacement of the dual chirality helix 1937. This in turn rotates the junction point 114 of the proximal helix 113 and the distal helix 112 and subsequent rotation of the distal segment 115. The degree of rotation is proportional to the linear displacement of the dual chirality helix 1937 of the tube 111. For illustration purposes 180 degree rotation is shown.

In some embodiments, a single helix 203 (see FIGS. 23-25) can be used as an alternative to the dual chirality helix 1937 in the medical device 110, such that the magnetic elements 117, 118 may be disposed on or in the tube 111 in contact with opposite ends of the single helix 203 to realize elongation or compression of the single helix 203 to impart rotational motion on the distal segment 115 and/or the distal end of the tube 111. Similarly, this rotational motion may be imparted to the distal end of the tube 201 in FIGS. 25A and 25B when magnetic elements 117, 118 are disposed in the device 200 in substantially or identically the same position as in FIGS. 19A and 19B.

Figure 20A:
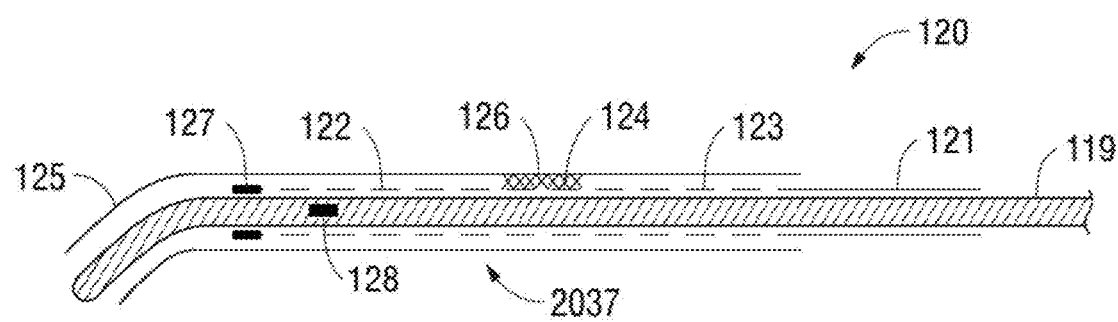
FIG. 20A is a longitudinal cross sectional view of the distal aspect of another embodiment of the medical device with a magnetic displacement mechanism in its resting state where one of the magnetic forces is provided via shaft with a magnetic element.

FIG. 20A is a longitudinal cross sectional view of the distal aspect of an embodiment of the medical device 120 in its resting state. The distal aspect of the medical device 120 is shown with a tube 121 with a distal end and a proximal end (wherein a dual chirality helix 2037 is cut into the distal aspect of the tube 121 to form a proximal helix 123 and a distal helix 122), a tube magnetic element 127, a guidewire magnetic element 128, and a distal segment 125 that is coupled to the junction point 124 of the two helices 122, 123 of the dual chirality helix 2037. The proximal helix 123 and the distal helix 122 are formed such that they have opposite orientations. For example, if the proximal helix 123 has a left handed orientation then the distal helix 122 has a right handed orientation or vice versa. By its nature, the junction point 124 of the left and right handed helices rotates when the ends of the dual chirality helix 2037 are linearly extended or retracted, resulting in the conversion of linear movement to rotational motion of the junction point 124 of the two helices. The distal segment 125 is located circumferentially around the distal aspect of the tube 121 in which the dual chirality helix 2037 is cut. The distal segment 125 is coupled to the junction 124 of the helices 122, 123 of the dual chirality helix 2037 via a coupling means 126. The distal segment 125 may have an angulated tip so as to aid in improved navigation of the medical device 120. The magnetic elements 127, 128 may include one or more of: a permanent magnet and an electromagnet. In some embodiments, one or both of the magnetic elements 127, 128 may be a rare earth magnet. The tube magnetic element 127 may comprise the same or a different magnetic element as the guidewire magnetic element 128. The magnetic elements 127, 128 may be configured to impart attractive or repulsive force between each other to impart linear displacement on the dual chirality helix 2037.

Figure 20B:
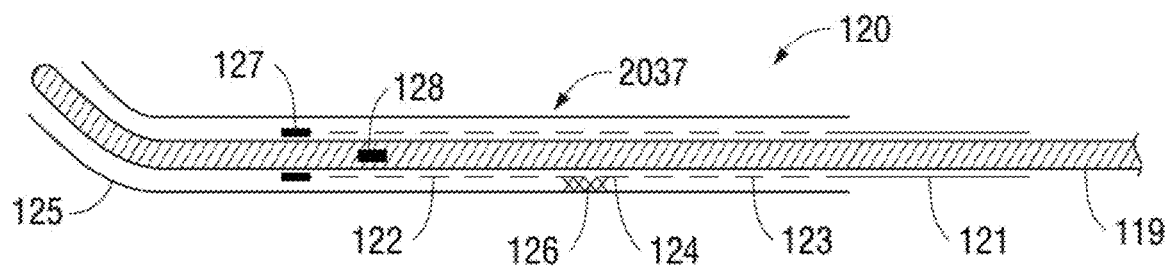
FIG. 20B is a longitudinal cross sectional view of the distal aspect of the medical device with the magnetic displacement mechanism of FIG. 20A with linear displacement of the dual chirality helix secondary magnetic forces imparted on the tube via shaft with a magnetic element.

FIG. 20B demonstrates linear displacement of the dual chirality helix 2037 when there is either 1) a change in the magnetic field of the either the tube magnetic element 127 or the guidewire magnetic element 128 or 2) a change in the distance between the tube magnetic element 127 and the guidewire magnetic element 128. The linear displacement causes the rotation of the junction point 124 of the proximal helix 123 and the distal helix 122 and subsequent rotation of the distal segment 125. The degree of rotation is proportional to the linear displacement of the dual chirality helix 2037 of the tube 121. For illustration purposes 180 degree rotation is shown.

Figure 21A:
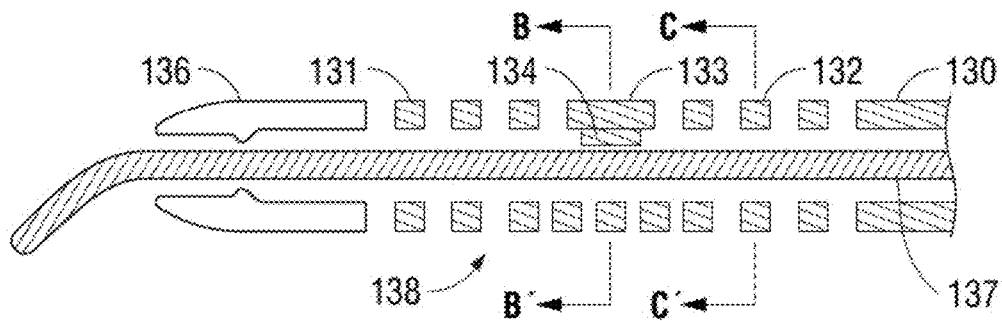
FIG. 21A is a longitudinal cross sectional view of the distal aspect of the medical device with a tooth-gear interface between a guidewire and the tube with no force applied to the distal end of the dual chirality helix.

FIG. 21A is a longitudinal cross sectional view of the distal aspect of another embodiment of the device in its resting state. The distal aspect of the device is shown with a tube 130 with a distal end and a proximal end, wherein a dual chirality helix 138 is cut into the distal aspect of the tube 130 to form a proximal helix 132 and a distal helix 131, and a guidewire 137 located within the lumen of the tube 130. The tube 130 can be made of one or more of a variety of materials, including, but not limited to, polyimide, polyurethane, polyether block amides (such as Pebax®), nylon, nickel titanium (nitinol), stainless steel braiding, coiled wire and hollow helical stranded tubing. The proximal helix 132 and the distal helix 131 are formed such that they have opposite orientations. For example, if the proximal helix 132 has a left handed orientation then the distal helix 131 has a right handed orientation or vice versa. By its nature, the junction point 133 of the left and right handed helices 131, 132 rotates when the ends of the dual chirality helix 138 are linearly extended or retracted, resulting in the conversion of linear movement to rotational motion of the junction point 133 of the two helices. The tube 130 has a reduced inner diameter 136 along its distal aspect. The distal aspect of the guidewire 137 has a reduced diameter. The inner diameter of the distal end of the tube 130 is greater than the diameter of the distal aspect of the guidewire 137 but less than the non-reduced diameter of the guidewire 137. The guidewire 137 may include one or more grooves 135 that located along the longitudinal axis of the guidewire 137. An engagement means 134 for engaging the guidewire 137, such as a tooth 134 is disposed between the guidewire 137 and the tube 130 at the junction point 133 of the dual chirality helix 138. The tooth 134 slidably engages one or more of the grooves 135 along the distal aspect of the guidewire 137. FIG. 21B shows a short axis cross section through line B-B' of FIG. 21A, which passes through the tube at the junction point 133. The tooth 134 is shown protruding from the tube 130 at the junction point 133 and meshing with one of the grooves 135 in the guidewire 137. FIG. 21C shows a short axis cross section through line C-C' of FIG. 21A, which passes through the proximal helix 132 of the tube 130. Advancing the guidewire 137 into the tube 130 results in linear displacement of the dual chirality helix 138. This in turn results in rotation of the junction point 133 and tooth 134 and subsequent rotation of the distal aspect of the guidewire 137 as depicted in FIGS. 22A and 22B.

Figure 22A:
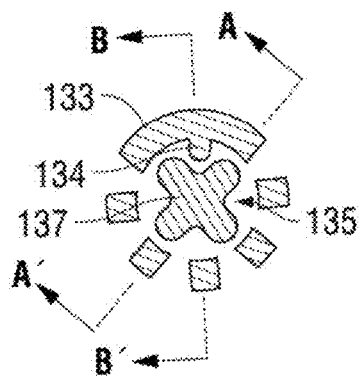
FIG. 22A is a longitudinal cross sectional view of the distal aspect of the guidewire at the level of the tooth-gear interface when the dual chirality helix undergoes longitudinal displacement.
Figure 22A:
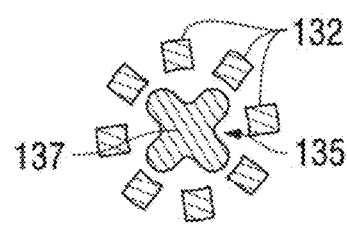
Figure 22A:
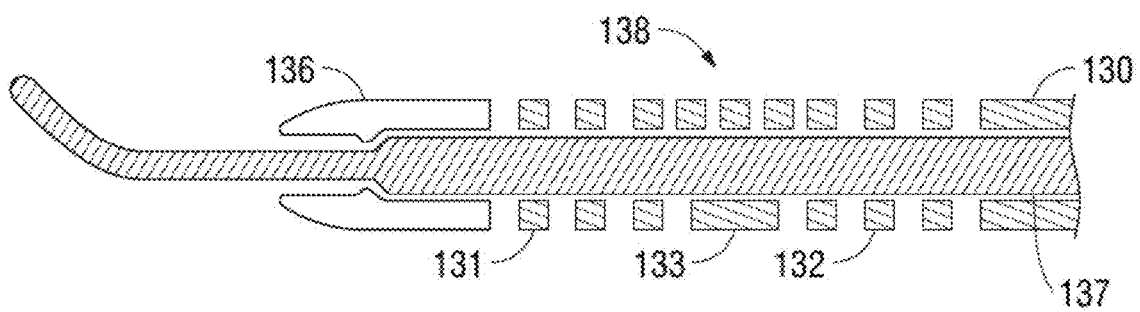
Figure 22B:
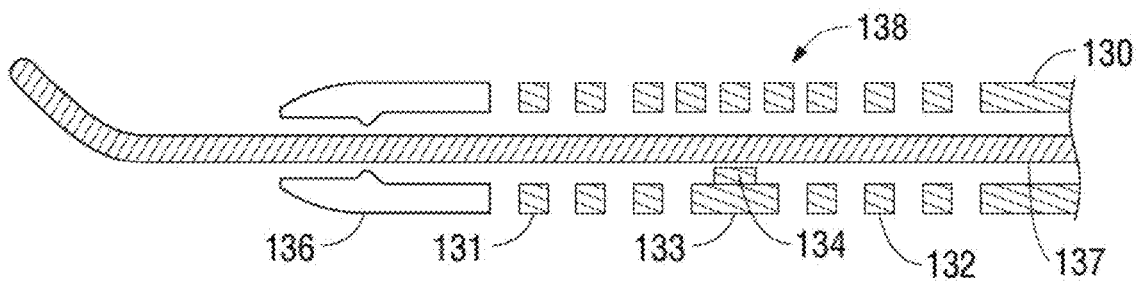
FIG. 22B is a longitudinal cross sectional view of the distal aspect of the guidewire at the level of the tooth-gear interface when the dual chirality helix undergoes longitudinal displacement.

FIG. 22A shows a longitudinal cross sectional view through line A-A' in FIG. 21B when the dual chirality helix 138 is displaced. FIG. 22B shows a longitudinal cross sectional view through line B-B' in FIG. 21B when the dual chirality helix 138 is displaced. The degree of rotation is proportional to the displacement of the dual chirality helix 138 of the tube 130.

FIG. 23a shows a medical device 200 according to another embodiment of the present disclosure. The device 200 includes a tube 201, a longitudinal displacer such as a sleeve 202, and a handle 270 that is attached to the proximal end of the tube 201. A helical or spiral cut 203 is present in the distal aspect of the tube 201 wherein the helical or spiral cut 203 has a cut width 208 and helical angle 209. The end of the tube 201 distal to the helical cut 203 may include a curve to aid in navigating the medical device 200 through the vasculature. The cut width 208 can range from 0.1 micrometers to 30 millimeters. In some embodiments, the cut width may range from about 0.1 millimeters to about 10 millimeters. The helical angle can range from 10 to 80 degrees relative to the longitudinal axis of the tube 201. In some embodiments, the helical angle range from 15 to 75 degrees. The sleeve 202 is disposed within the lumen of the tube 201. The tube 201 may have a reduced inner diameter on the distal end to form a shelf 204 that prevents forward movement of the sleeve 202. In some embodiments, the sleeve 202 may abut the shelf 204 to transmit longitudinal force from the sleeve 202 to the tube 201. In some embodiments, the sleeve 202 may be coupled to the tube 201 at a point distal to the helical or spiral cut 203, such as at the shelf 204, and can be advanced or retracted within the tube 201 wherein advancement or retraction of the sleeve 202 results in advancement or retraction of the tube 201 distal to the helical or spiral cut 203. In some embodiments, the coupling means may be reversible, such as a solder connection that can be melted by application of electric current or heat to release the sleeve 202 from the tube 201. Means of coupling the sleeve 202 and tube 201 include, but are not limited to, one or more of: 1) frictional fit, 2) adhesives (such as cyanoacrylate), 3) welding, 4) brazing, 5) soldering, and 6) mechanical linking. As depicted in FIG. 23f the device 200 also includes a handle 270, which is comprised of a proximal component 271 and a distal component 272 and is attached to the proximal end of the tube 201. The proximal component 271 and the distal component 272 each have cylindrical bodies, such that the proximal component 271 may be inserted into the distal component 272 and the sleeve 202 may be inserted into the proximal component 271. The proximal component 271 is reversibly coupled to the sleeve 202 and the distal component 272 is reversibly coupled to the tube 201. Each of the tube, 201 and the sleeve 202 can be made of one or more of a variety of materials, including, but not limited to, polyimide, polyurethane, polyether block amides (such as Pebax®), nylon, nitinol, stainless steel braiding, coiled wire and hollow helical stranded tubing. The lumen of the tube 201 and outer surface of the sleeve 202 preferentially have a low coefficient of friction, including but not limited to PTFE or a hydrophilic coating. In addition the distal aspect of the tube 201 may have, but is not limited to, a straight, angled, and reverse curved shape. FIG. 23c is an axial cross section through line C-C' in FIG. 23a. FIG. 23d is an axial cross section through line D-D' in FIG. 23a. FIG. 23b is a longitudinal cross section of the device 200 in FIG. 23a. FIG. 23e is an axial cross section through line E-E' in FIG. 23a.

Figure 24A:
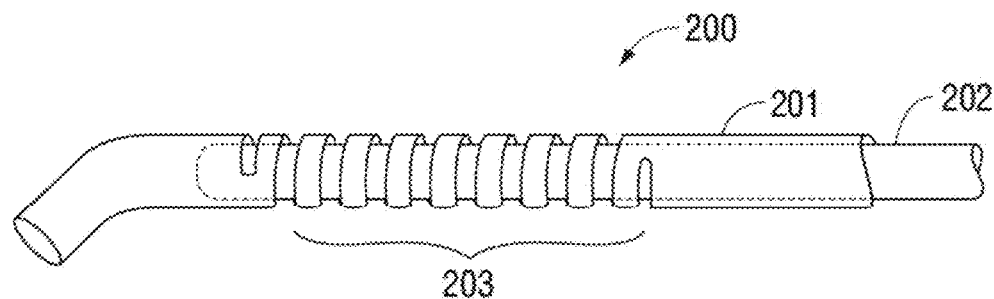
FIG. 24A is a diagram of the catheter of FIG. 23A at rest (no longitudinal force) with a distal member.
Figure 24B:
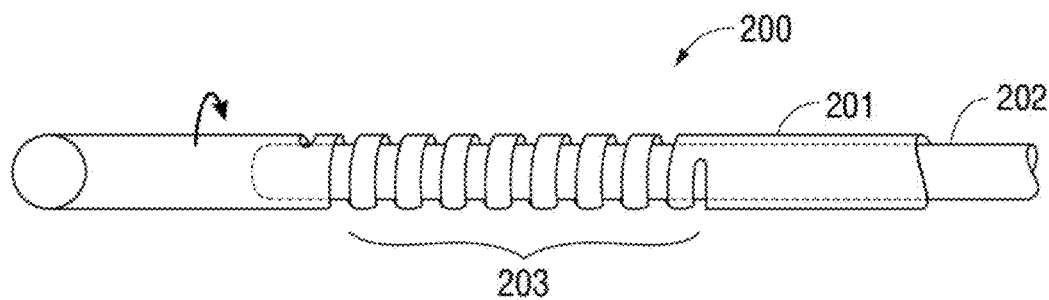
FIG. 24B is a diagram of the catheter of FIG. 23A with longitudinal force at the proximal end causing a rotation of the distal end by 90 degrees.
Figure 24C:
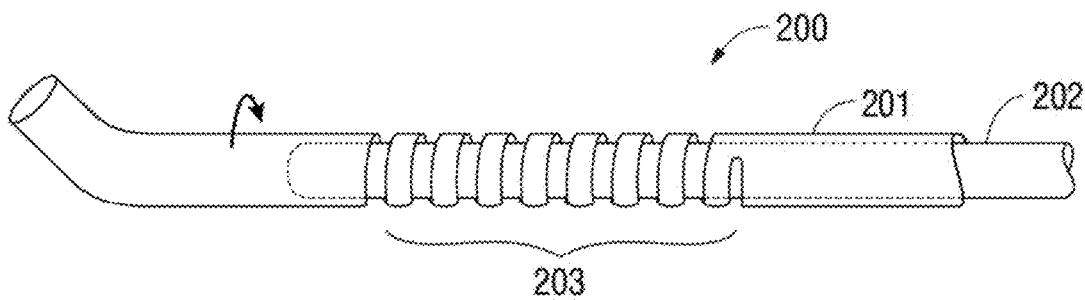
FIG. 24c is a diagram of the catheter of FIG. 23A with longitudinal force at the proximal end causing a rotation of the distal end by 180 degrees.
Figure 24D:
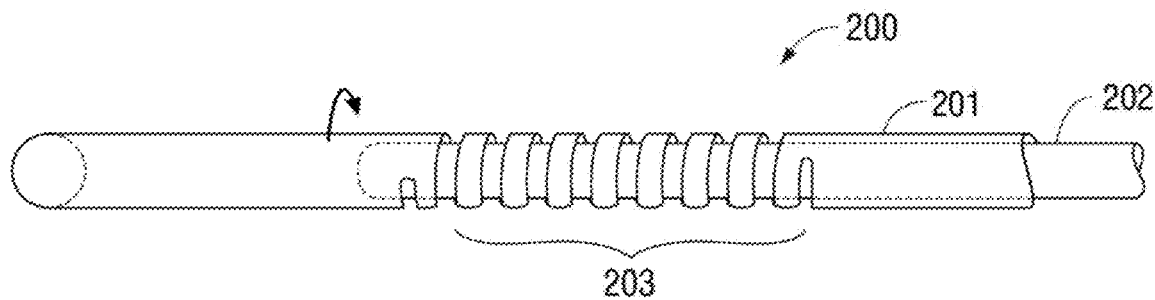
FIG. 24d is a diagram of the catheter of FIG. 23A with longitudinal force at the proximal end causing a rotation of the distal end by 270 degrees.

FIG. 24a shows the device 200 wherein the device 200 is in its resting state (no longitudinal displacement) of the distal end of the tube 201. FIG. 24b shows the device 200 wherein there is longitudinal displacement of the distal end of the tube 201 by advancement of the sleeve 202 such that the distal end of the tube 201 results in 90 degrees of rotation relative to the position of the distal end of the tube 201 in FIG. 24A. FIG. 24c shows the device 200 wherein there is further longitudinal displacement of the distal end of the tube 201 by advancement of the sleeve 202 such that the distal end of the tube 201 results in 180 degrees of rotation relative to the position of the distal end of the tube 201 in FIG. 24A. FIG. 24d shows the device 200 wherein there is further longitudinal displacement of the distal end of the tube 201 by advancement of the sleeve 202 such that the distal end of the tube 201 results in 270 degrees of rotation relative to the distal position of the tube 201 in FIG. 24A.

Figure 25A:
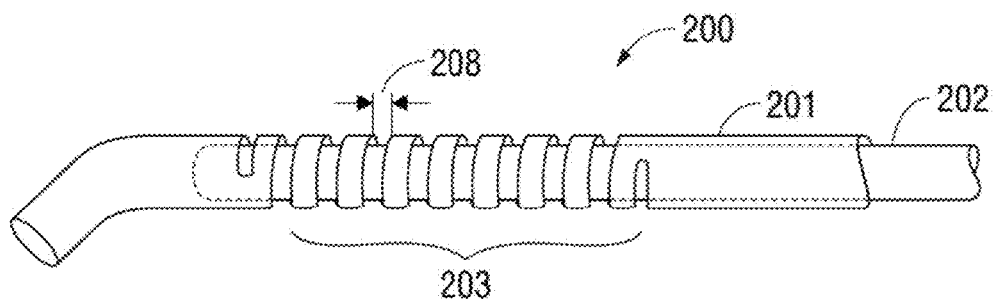
FIG. 25A is a diagram of the catheter of FIG. 23A while in its resting state (0 degrees of rotation)
Figure 25B:
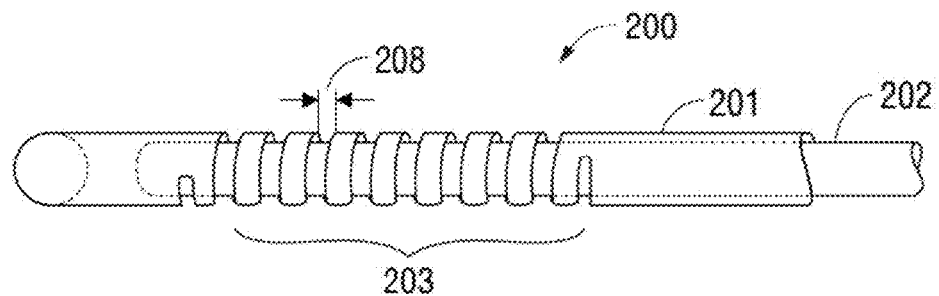
FIG. 25B is a diagram of the catheter of FIG. 23A when the sleeve is retracted to reverse the rotation of the distal end to −90 degrees.

FIG. 25a shows the device 200 wherein there device 200 is in its resting state (no longitudinal displacement) of the distal end of the tube 201. FIG. 25b shows the device 200 wherein there is longitudinal displacement of the distal end of the tube 201 by retraction of the sleeve 202 such that the distal end of the tube 201 results in −90 degrees of rotation.

It will now be evident to those skilled in the art that there has been described herein methods and apparatuses for improved rotation of the distal aspect of a device. Although the invention hereof has been described by way of several embodiments, it will be evident that other adaptations and modifications can be employed without departing from the spirit and scope thereof. The terms and expressions employed herein have been used as terms of description and not of limitation; and thus, there is no intent of excluding equivalents, but on the contrary it is intended to cover any and all equivalents that may be employed without departing from the spirit and scope of the invention.

While the disclosure has been described with reference to exemplary embodiments, it will be understood that various changes may be made and equivalents may be substituted for elements thereof without departing from the scope of the disclosure. In addition, many modifications will be appreciated to adapt a particular instrument, situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

What is claimed is:

1. A device comprising:
   a tube with a longitudinal axis having a proximal end and a distal end;
   at least one partial cut located at, along or near the distal end of the tube, the at least one partial cut comprising an orientation that is angled relative to both the longitudinal axis and an axis transverse to the longitudinal axis;
   a pusher member slidably positioned within a lumen of the tube and configured to impart a force along the at least one partial cut of the tube, wherein the distal end of the tube is configured to at least partially rotate relative to the longitudinal axis when the pusher member imparts a force along the at least one partial cut of the tube; and
   an expandable member;
   wherein the pusher member is configured to selectively engage at least a portion of the tube along the distal end using the expandable member, the pusher member configured to impart a force along the at least one partial cut of the tube when the pusher member engages the tube and the pusher member is moved relative to the tube to cause the distal end of the tube to at least partially rotate relative to the longitudinal axis; and
   wherein a degree of rotation of the distal end of the tube is proportional to a linear displacement of the at least one partial cut.

2. The device of claim 1, wherein the at least one partial cut extends throughout an entire thickness of a wall of the tube.

3. The device of claim 1, wherein the at least one partial cut does not extend throughout an entire thickness of a wall of the tube.

4. The device of claim 1, wherein the at least one partial cut comprises a spiral or helical shape.

5. The device of claim 4, wherein an angle of the at least one partial cut relative to the longitudinal axis is between 10 and 80 degrees.

6. The device of claim 1, wherein the pusher member is configured to selectively engage at least a portion of the tube along the distal end of the tube using the expandable member.

7. The device of claim 6, wherein the expandable member comprises a reversibly expandable member.

8. The device of claim 6, wherein the expandable member is positioned at least partially radially between the tube and the pusher member along the distal end of the tube.

9. The device of claim 1, wherein the pusher member comprises a lumen.

10. The device of claim 1, wherein the pusher member comprises a wire.

11. A device comprising:
    a first member with a longitudinal axis having a proximal end and a distal end;
    at least one partial cut located at, along or near the distal end of the first member, the at least one partial cut comprising an orientation that is angled relative to both the longitudinal axis and an axis transverse to the longitudinal axis; and a second member positioned adjacent the first member and configured to impart a force along the at least one partial cut of the first member, wherein the distal end of the first member is configured to at least partially rotate relative to the longitudinal axis when the second member imparts a force along the at least one partial cut of the first member;

wherein the second member is configured to selectively engage at least a portion of the first member along the distal end, the second member configured to impart a force along the at least one partial cut of the first member when the second member engages the first member and the second member is manipulated to cause the distal end of the first member to at least partially rotate relative to the longitudinal axis; and wherein a degree of rotation of the distal end of the first member is proportional to a linear displacement of the at least one partial cut.

12. The device of claim 11, wherein the at least one partial cut extends throughout an entire thickness of a wall of the first member.

13. The device of claim 11, wherein the at least one partial cut does not extend throughout an entire thickness of a wall of the first member.

14. The device of claim 11, wherein the at least one partial cut comprises a spiral or helical shape.

15. The device of claim 14, wherein an angle of the at least one partial cut relative to the longitudinal axis is between 10 and 80 degrees.

16. The device of claim 11, wherein the second member is configured to selectively engage at least a portion of the first member using an expandable member.

17. The device of claim 16, wherein the expandable member comprises a reversibly expandable member.

18. The device of claim 16, wherein the expandable member is positioned radially between the first member and the second member along the distal end of the first member.

19. The device of claim 11, wherein the second member comprises a lumen.

20. The device of claim 11, wherein the first member comprises a tube and the second member comprises a wire.

* * * * *

UNITED STATES PATENT AND TRADEMARK OFFICE
CERTIFICATE OF CORRECTION

| | |
|---|---|
| PATENT NO. | : 11,717,641 B2 |
| APPLICATION NO. | : 16/551454 |
| DATED | : August 8, 2023 |
| INVENTOR(S) | : Brian Giles |

It is certified that error appears in the above-identified patent and that said Letters Patent is hereby corrected as shown below:

In the Specification

In Column 7, Line 26, delete "the a" and insert --the--.

In Column 12, Line 65, delete "12A." and insert --12A;--.

In Column 13, Line 13 (Approx.), delete "15A." and insert --15A;--.

In Column 13, Line 16 (Approx.), delete "15A." and insert --15A;--.

In Column 20, Line 34, delete "the a" and insert --the--.

Signed and Sealed this
Twelfth Day of December, 2023

Katherine Kelly Vidal
*Director of the United States Patent and Trademark Office*